(12) United States Patent
Yang et al.

(10) Patent No.: US 12,428,433 B2
(45) Date of Patent: Sep. 30, 2025

(54) FLUORINE-CONTAINING HETEROCYCLIC DERIVATIVES WITH MACROCYCLIC STRUCTURE AND USE THEREOF

(71) Applicant: ScinnoHub Pharmaceutical Co., Ltd, Sichuan (CN)

(72) Inventors: Anle Yang, Sichuan (CN); Haoxi Huang, Sichuan (CN); Tonghui Chen, Sichuan (CN); Jie Liang, Sichuan (CN); Dewei Zhang, Sichuan (CN); Jingen Deng, Sichuan (CN); Hongbo Li, Sichuan (CN); Junjie Pu, Sichuan (CN)

(73) Assignee: SCINNOHUB PHARMACEUTICAL CO., LTD, Sichuan (CN)

( * ) Notice: Subject to any disclaimer, the term of this patent is extended or adjusted under 35 U.S.C. 154(b) by 793 days.

(21) Appl. No.: 17/781,167

(22) PCT Filed: Dec. 11, 2020

(86) PCT No.: PCT/CN2020/135526
§ 371 (c)(1),
(2) Date: May 31, 2022

(87) PCT Pub. No.: WO2021/115401
PCT Pub. Date: Jun. 17, 2021

(65) Prior Publication Data
US 2023/0044722 A1   Feb. 9, 2023

(30) Foreign Application Priority Data

Dec. 13, 2019 (CN) .......................... 201911285488.6
Jan. 15, 2020 (CN) .......................... 202010040378.X
Nov. 2, 2020 (CN) .......................... 202011200880.9

(51) Int. Cl.
*C07D 498/22* (2006.01)

(52) U.S. Cl.
CPC ........ *C07D 498/22* (2013.01); *C07B 2200/07* (2013.01)

(58) Field of Classification Search
CPC .......................... C07D 498/22; C07B 2200/07
See application file for complete search history.

(56) References Cited

FOREIGN PATENT DOCUMENTS

| CN | 102971322 A | | 3/2013 |
| CN | 107735399 A | | 2/2018 |
| WO | 2011146336 A1 | | 11/2011 |
| WO | 2019210835 A1 | | 11/2019 |
| WO | WO 2019/210835 | * | 11/2019 ........... C07D 487/04 |

OTHER PUBLICATIONS

Int'l Search Report issued Mar. 10, 2021 in Int'l Application No. PCT/CN2020/135526.

* cited by examiner

*Primary Examiner* — Erich A Leeser
(74) *Attorney, Agent, or Firm* — Panitch Schwarze Belisario & Nadel LLP

(57) ABSTRACT

Disclosed are a macrocyclic fluorine-containing heterocyclic derivative of formula (I), a preparation method thereof, and a use thereof in treatment of TRK kinase-mediated diseases.

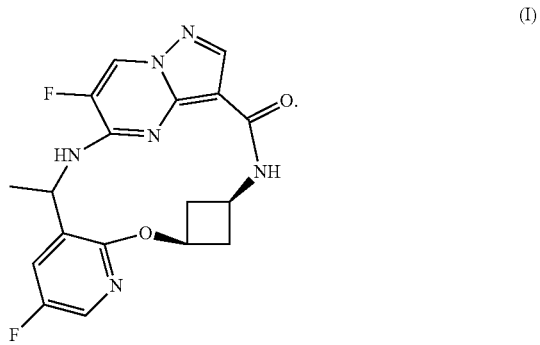

4 Claims, 1 Drawing Sheet

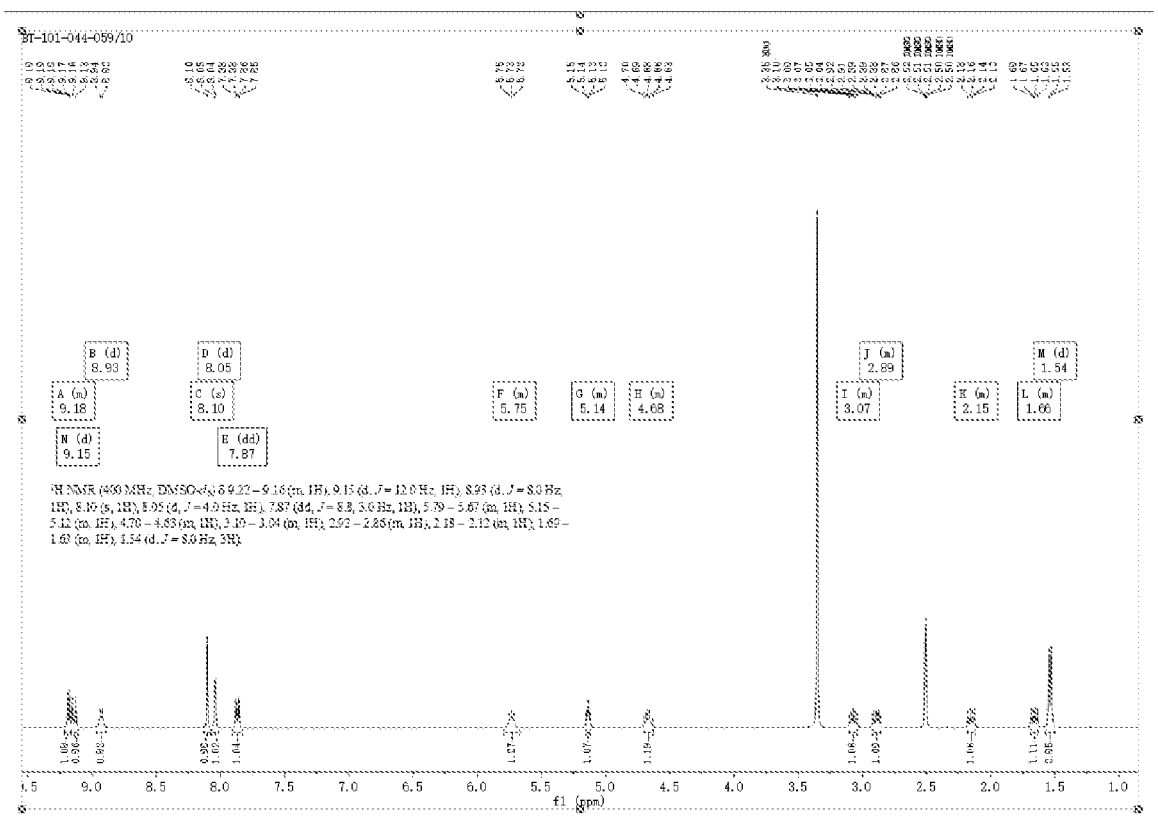

FLUORINE-CONTAINING HETEROCYCLIC DERIVATIVES WITH MACROCYCLIC STRUCTURE AND USE THEREOF

CROSS-REFERENCE TO RELATED APPLICATIONS

This application is a Section 371 of International Application No. PCT/CN2020/135526, filed Dec. 11, 2020, which was published in the Chinese language on Jun. 17, 2021, under International Publication No. WO 2021/115401 A1, which claims priority under 35 U.S.C. § 119 (b) to Chinese Application No. 201911285488.6, filed Dec. 13, 2019, Chinese Application No. 202010040378.X, filed Jan. 15, 2020, and Chinese Application No. 202011200880.9, filed on Nov. 2, 2020, the disclosure of each of which is incorporated herein by reference in its entirety.

TECHNICAL FIELD

The present application relates to a macrocyclic fluorine-containing heterocyclic derivative, a preparation method thereof, and a use thereof in treatment of TRK kinase-mediated diseases, and belongs to the field of medical chemistry.

BACKGROUND OF THE INVENTION

NTRK/TRK (Tropoyosin receptor kinase) is a neurotrophic factor tyrosine kinase receptor, and belongs to a receptor tyrosine kinase family. NTRK genes of tyrosine kinase contain NTRK1, NTRK2 and NTRK3, which are respectively responsible for encoding proteins TRKA, TRKB and TRKC of a tropomyosin receptor kinase (TRK) family for synthesizing. The combination of the neurotrophic factor with the TRK proteins may induce receptor dimerization and phosphorylation, and activate downstream PI3K, RAS/MAPK/ERK and PLC-γ signal cascade pathways. The TRK kinase plays important physiological roles in the development of nerve, comprising the growth and function maintenance of neuron axon, the occurrence and development of memory and the protection of neuron from injury. However, the change of TRK signal pathway comprises gene fusion, protein over-expression or single nucleotide change, which has been found to be the pathogenic cause of many tumors, especially the fusion of NTRK genes is the most definite carcinogenic cause at present. The NTRK is found in lung cancer, head and neck cancer, breast cancer, thyroid cancer, glioma and other tumors, such as CD74-NTRK1, MPRIP-NTRK1, QKINTRK2, ETV6-NTRK3, and BTB1-NTRK3. Although an incidence rate in common lung cancer and colorectal cancer is less than 5%, this pathway is shared in the pathogenesis of various cancers, and current clinical trial drugs may cover the universal cancer treatment of NTRK+. Therefore, in recent years, a TRK fusion protein has become an effective anti-cancer target and a research hotspot.

Larotrectinib of LOXO Oncology Company, granted with an orphan drug qualification, a breakthrough therapy and a rare disease treatment drug as a first generation TRK inhibitor, was submitted to FDA, and the present application was completed in March 2018, and appeared on the market at the end of 2018. According to data presented at American Society for Clinical Oncology (AMSO), Larotrectinib is the first choice to treat cancer patients with TRK gene mutation and the first "broad-spectrum targeted drug" appearing on the market. In addition, the researches on related targets further comprise Entrectinib of Ignyta Company, ONO-7579 of Ono Pharmaceutical Company and TPX-0005 of TP Therapeutics Company respectively, and all drugs are currently in a clinical research stage. However, after receiving TRK inhibitor treatment, some mutations (such as mutations at NTK1 G595R, NTRK3 G623R and other sites) may occur in TRK genes of the cancer patients, resulting in drug resistance, and the patients in this period need a new therapeutic drug. It is expected to solve the problem of tumor drug resistance caused by NTRK mutation by finding a new TRK kinase inhibitor. At present, there is a second generation TRK inhibitor LOXO-195 jointly developed by Bayer and LOXO Oncology companies for the mutation problem, and this drug is undergoing a phase II clinical trial. At present, LOXO-195 is clinically administrated twice a day in research.

At present, literatures about the TRK inhibitor have been reported one after another, such as WO2011/146336, which discloses a macrocyclic compound as a TRK kinase inhibitor, but it is not considered that the specific description in the WO2011/146336 patent is a part of the present application.

BRIEF SUMMARY OF THE INVENTION

A compound provided by the present application has unexpected technical effects in biological activity, especially in-vitro drug efficacy on mutations at NTRK1 G595R, NTRK3 G623R and other sites, stability in liver microsomes of human, rat and mouse, drug metabolism, and oral bioavailability.

The present application provides a compound of formula (I), a tautomer, a mesomer, a racemate, an enantiomer, a diastereomer or a mixture thereof, or a pharmaceutically acceptable salt thereof:

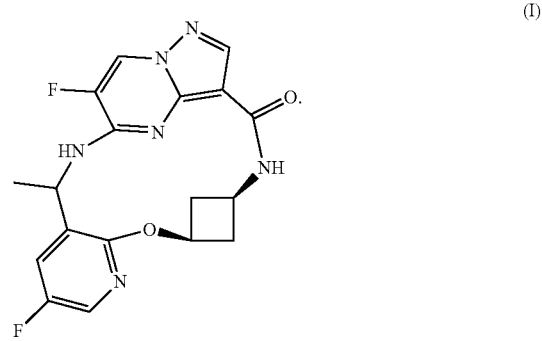 [SMILES: CC1Nc2nc3c(cnn3cc2F)C(=O)N[C@H]2C[C@H](C2)Oc2ncc(F)cc21]

The embodiments of the present application also provide a compound of formula (Ia), a tautomer, a mesomer, a racemate, an enantiomer, a diastereomer or a mixture thereof, or a pharmaceutically acceptable salt thereof:

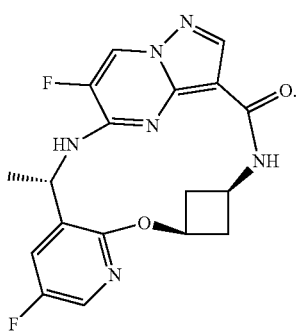

(Ia)

The embodiments of the present application also provide a compound of formula (Ib), a tautomer, a mesomer, a racemate, an enantiomer, a diastereomer or a mixture thereof, or a pharmaceutically acceptable salt thereof:

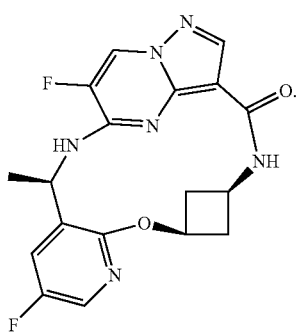

(Ib)

The embodiments of the present application also provide a pharmaceutical composition, comprising the compound, the tautomer, the mesomer, the racemate, the enantiomer, the diastereomer or the mixture thereof, or the pharmaceutically acceptable salt thereof according to the present application, and a pharmaceutically acceptable diluent or carrier.

In some embodiments, in the pharmaceutical composition of the present application, the compound, the tautomer, the mesomer, the racemate, the enantiomer, the diastereomer or the mixture thereof, or the pharmaceutically acceptable salt thereof according to the present application is presented in an effective amount for treating a disease or an illness.

The embodiments of the present application also provide a use of the compound, the tautomer, the mesomer, the racemate, the enantiomer, the diastereomer or the mixture thereof, or the pharmaceutically acceptable salt thereof according to the present application, or the pharmaceutical composition above in preparation of a drug for treating a disease or an illness, wherein the disease or the illness is selected from pain, cancer, inflammation and neurodegenerative diseases.

The embodiments of the present application provide a use of the compound, the tautomer, the mesomer, the racemate, the enantiomer, the diastereomer or the mixture thereof, or the pharmaceutically acceptable salt thereof according to the present application, or the pharmaceutical composition comprising the compound of the present application in preparation of a drug as a TRK kinase inhibitor.

The embodiments of the present application provide a use of the compound, the tautomer, the mesomer, the racemate, the enantiomer, the diastereomer or the mixture thereof, or the pharmaceutically acceptable salt thereof according to the present application, or the pharmaceutical composition comprising the compound of the present application in inhibition of an activity of a TRK kinase.

The embodiments of the present application provide a use of the compound, the tautomer, the mesomer, the racemate, the enantiomer, the diastereomer or the mixture thereof, or the pharmaceutically acceptable salt thereof according to the present application, or the pharmaceutical composition comprising the compound of the present application in treatment of a disease or an illness, wherein the disease or the illness is selected from pain, cancer, inflammation and neurodegenerative diseases.

The embodiments of the present application also provide the compound, the tautomer, the mesomer, the racemate, the enantiomer, the diastereomer or the mixture thereof, or the pharmaceutically acceptable salt thereof according to the present application, or the pharmaceutical composition comprising the compound of the present application for inhibiting the activity of the TRK kinase.

The embodiments of the present application also provide the compound, the tautomer, the mesomer, the racemate, the enantiomer, the diastereomer or the mixture thereof, or the pharmaceutically acceptable salt thereof according to the present application, or the pharmaceutical composition comprising the compound of the present application for treating the disease or the illness, wherein the disease or the illness is selected from pain, cancer, inflammation and neurodegenerative diseases.

The embodiments of the present application also provide the compound, the tautomer, the mesomer, the racemate, the enantiomer, the diastereomer or the mixture thereof, or the pharmaceutically acceptable salt thereof according to the present application, or the pharmaceutical composition comprising the compound of the present application as the TRK kinase inhibitor.

One or more embodiments of the present application provide a treatment method of a disease or an illness, comprising: administering the compound, the tautomer, the mesomer, the racemate, the enantiomer, the diastereomer or the mixture thereof, or the pharmaceutically acceptable salt thereof according to the present application, or the pharmaceutical composition comprising the compound of the present application to a subject in need thereof. In some embodiments, the disease or the illness is selected from pain, cancer, inflammation and neurodegenerative diseases. In some embodiments, the method comprises administering an effective amount of the compound, the tautomer, the mesomer, the racemate, the enantiomer, the diastereomer or the mixture thereof, or the pharmaceutically acceptable salt thereof according to the present application, or the pharmaceutical composition comprising the compound of the present application to the subject in need thereof.

The embodiments of the present application also provide a composition for treating a disease or an illness, comprising the compound, the tautomer, the mesomer, the racemate, the enantiomer, the diastereomer or the mixture thereof, or the pharmaceutically acceptable salt thereof according to the present application, wherein the disease or the illness is selected from pain, cancer, inflammation and neurodegenerative diseases.

The embodiments of the present application also provide a composition for inhibiting an activity of a TRK kinase, comprising the compound, the tautomer, the mesomer, the racemate, the enantiomer, the diastereomer or the mixture thereof, or the pharmaceutically acceptable salt thereof according to the present application.

The embodiments of the present application also provide a drug for treating a disease or an illness, comprising the compound, the tautomer, the mesomer, the racemate, the enantiomer, the diastereomer or the mixture thereof according to the present application as an active ingredient, wherein the disease or the illness is selected from pain, cancer, inflammation and neurodegenerative diseases.

The embodiments of the present application provide the compound, the tautomer, the mesomer, the racemate, the enantiomer, the diastereomer or the mixture thereof, or the pharmaceutically acceptable salt thereof according to the present application as a drug.

One or more embodiments of the present application provide the compound, the tautomer, the mesomer, the racemate, the enantiomer, the diastereomer or the mixture thereof, or the pharmaceutically acceptable salt thereof according to the present application for treating and/or inhibiting the disease or the illness.

In one or more embodiments, the disease or the illness above is the cancer.

In one or more embodiments, the cancer above is selected from neuroblastoma, ovarian cancer, colorectal cancer, melanoma, head and neck cancer, gastric cancer, lung cancer, breast cancer, glioblastoma, medulloblastoma, secretory breast cancer, salivary gland carcinoma, papillary thyroid cancer, adult myeloid leukemia, pancreatic cancer, prostate cancer, appendix cancer, cholangiocarcinoma, gastrointestinal stromal tumor and infantile fibrosarcoma.

The present application provides a compound of formula Ib-a or Ib-b or a salt thereof,

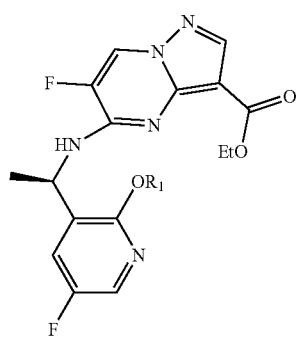

Ib-a

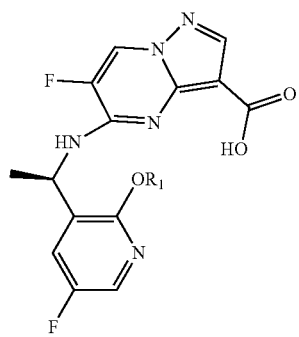

Ib-b wherein $R_1$ is selected from $C_1$-$C_3$ alkyl, and preferably, $R_1$ is selected from methyl or ethyl.

The present application also provides a compound of formula Ib-c or Ib-d or a salt thereof,

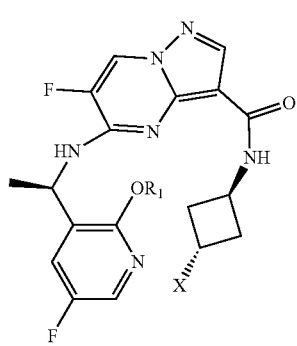

Ib-c

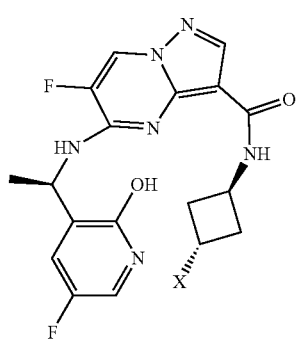

Ib-d wherein $R_1$ is $C_1$-$C_3$ alkyl, and X is halogen or

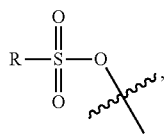

wherein R is selected from substituted or unsubstituted $C_1$-$C_4$ alkyl and a benzene ring, and the substituted $C_1$-$C_4$ alkyl or the benzene ring is substituted by one or more (for example, one to five) substituents selected from $C_1$-$C_4$ alkyl, nitryl, halogen and methoxy; and preferably, $R_1$ is methyl or ethyl, and X is halogen or

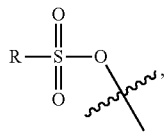

wherein R is methyl or p-tolyl.

In some embodiments, in the compound of formula Ib-a, formula Ib-b, formula Ib-c or formula Ib-d, $R_1$ is methyl, ethyl, n-propyl or isopropyl.

In some embodiments, in the compound of formula Ib-a, formula Ib-b, formula Ib-c or formula Ib-d, $R_1$ is methyl.

In some embodiments, in the compound of formula Ib-a, formula Ib-b, formula Ib-c or formula Ib-d, $R_1$ is ethyl.

In some embodiments, in the compound of formula Ib-a, formula Ib-b, formula Ib-c or formula Ib-d, X is halogen.

In some embodiments, in the compound of formula Ib-a, formula Ib-b, formula Ib-c or formula Ib-d, $R_1$ is n-propyl.

In some embodiments, in the compound of formula Ib-a, formula Ib-b, formula Ib-c or formula Ib-d, X is fluorine, chlorine, bromine or iodine.

In some embodiments, in the compound of formula Ib-a, formula Ib-b, formula Ib-c or formula Ib-d, X is

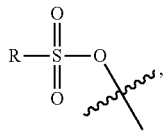

wherein R is $C_1$-$C_4$ alkyl.

In some embodiments, in the compound of formula Ib-a, formula Ib-b, formula Ib-c or formula Ib-d, X is

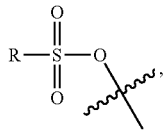

wherein R is methyl, ethyl, n-propyl, isopropyl, n-butyl, sec-butyl, isobutyl or tert-butyl.

In some embodiments, in the compound of formula Ib-a, formula Ib-b, formula Ib-c or formula Ib-d, X is

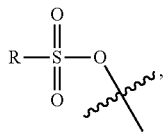

wherein R is methyl or p-tolyl.

In some embodiments, in the compound of formula Ib-a, formula Ib-b, formula Ib-c or formula Ib-d, X is

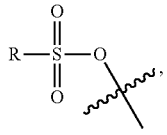

wherein R is methyl.

In some embodiments, in the compound of formula Ib-a, formula Ib-b, formula Ib-c or formula Ib-d, X is

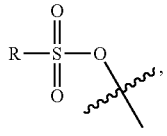

wherein R is p-tolyl.

Preferably, the compound of formula Ib-a, formula Ib-b, formula Ib-c or formula Ib-d provided by the present application has the following structure:

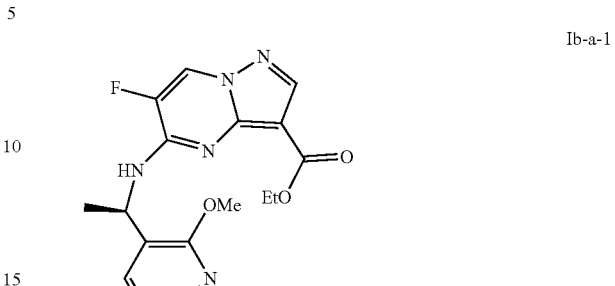

Ib-a-1

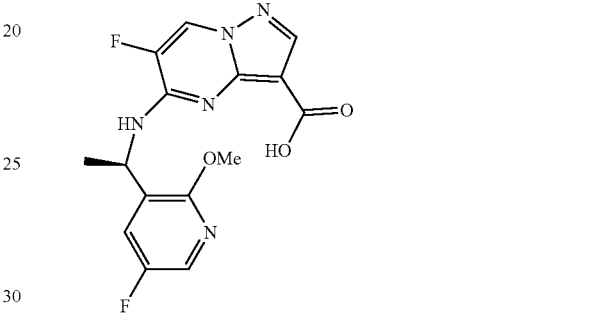

Ib-b-1

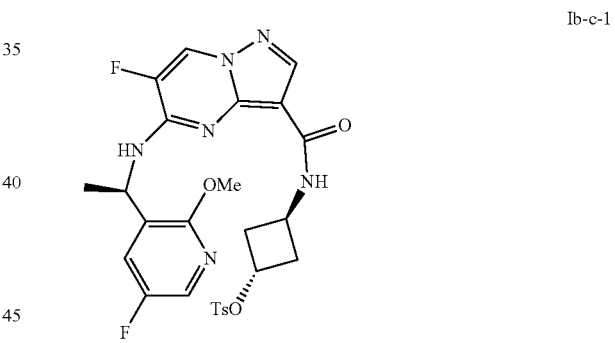

Ib-c-1

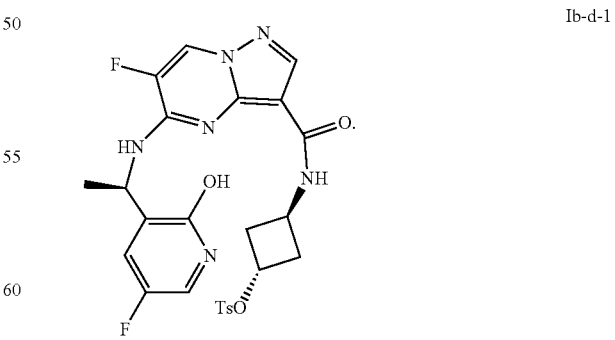

Ib-d-1

The present application provides a preparation method of a compound of formula Ib-a, comprising: subjecting a compound A and a compound B to a nucleophilic substitution reaction to obtain the compound of formula Ib-a:

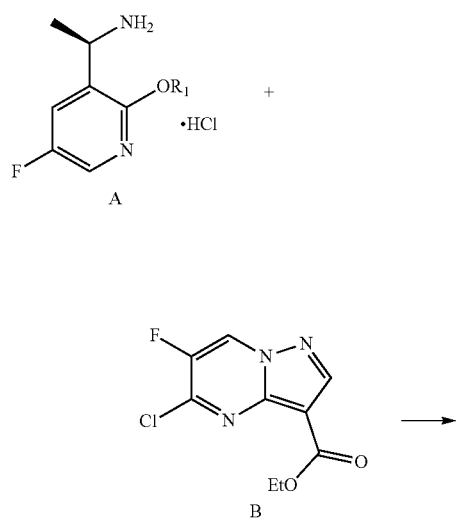

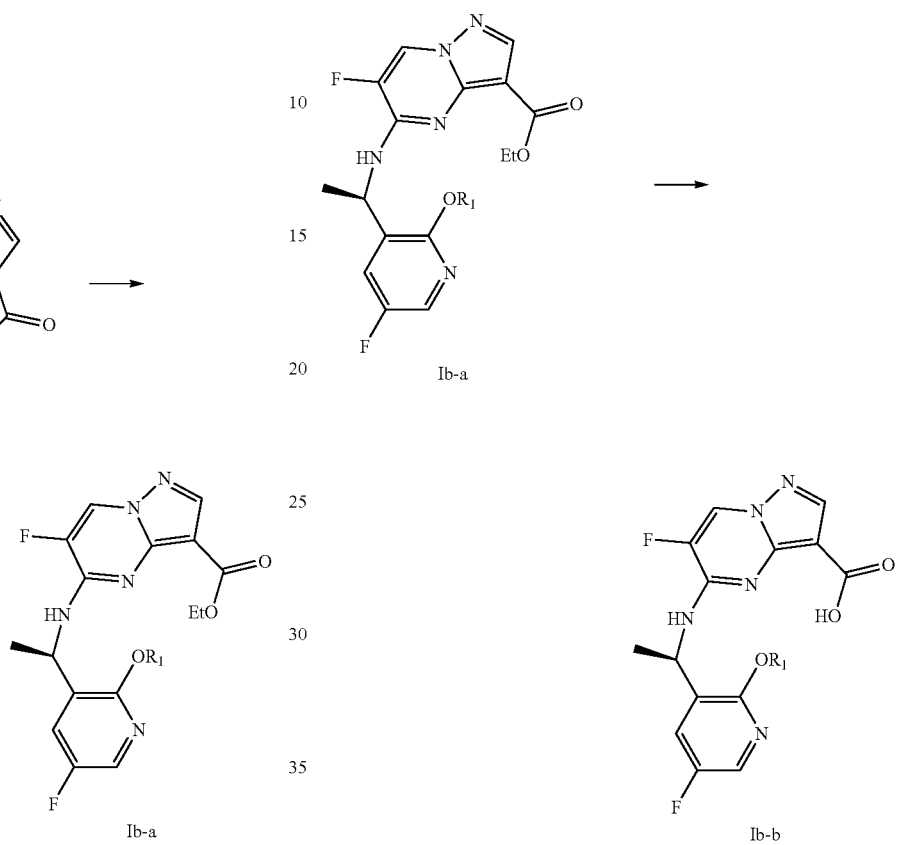

wherein $R_1$ is selected from $C_1$-$C_3$ alkyl; and preferably, $R_1$ is selected from methyl or ethyl.

Further, according to the preparation method of the compound of formula Ib-a of the present application, the reaction is carried out with alkali; preferably, the alkali is selected from one or more of TEA, DIPEA and DMAP; and further, the reaction is also carried out in a solvent of acetonitrile.

Further, according to the preparation method of the compound of formula Ib-a of the present application, the reaction is carried out at a temperature higher than 30° C., preferably, the reaction is carried out at a temperature of 50° C. to 60° C., and more preferably, the reaction is carried out at a temperature of 60° C.

In some embodiments, according to the preparation method of the compound of formula Ib-a provided by the present application, the nucleophilic substitution reaction is carried out in the presence of alkali; preferably, the alkali is selected from one or more of TEA, DIPEA and DMAP; and further preferably, the nucleophilic substitution reaction is carried out in a solvent, and preferably, the solvent is acetonitrile.

In some embodiments, according to the preparation method of the compound of formula Ib-a provided by the present application, the nucleophilic substitution reaction is carried out at a temperature higher than 30° C., preferably, the nucleophilic substitution reaction is carried out at a temperature of 50° C. to 60° C., and more preferably, the nucleophilic substitution reaction is carried out at a temperature of 60° C.

The present application provides a preparation method of a compound of formula Ib-b, comprising: hydrolyzing a compound of formula Ib-a to obtain the compound of formula Ib-b, wherein $R_1$ is selected from $C_1$-$C_3$ alkyl; and preferably, $R_1$ is selected from methyl or ethyl.

Preferably, according to the preparation method of the compound of formula Ib-b of the present application, the reaction is carried out with alkali; preferably, the alkali is selected from NaOH; and further, the reaction is carried out in a solvent of EtOH/H$_2$O, wherein $V_{(EtOH)}/V_{(H2O)} = 1/3$.

In some embodiments, according to the preparation method of the compound of formula Ib-b provided by the present application, the hydrolysis reaction is carried out in the presence of alkali, preferably, the alkali is NaOH; and further preferably, the hydrolysis reaction is carried out in a solvent, and preferably, the solvent is an EtOH/H$_2$O mixed solution, wherein $V_{(EtOH)}/V_{(H2O)} = 1/3$.

The present application provides a preparation method of a compound of formula Ib-c or a salt thereof, comprising: subjecting a compound of formula Ib-b and a compound C to an acid-amine condensation reaction to obtain the compound of formula Ib-c, wherein the compound C is

or a hydrochloride formed by the compound C:

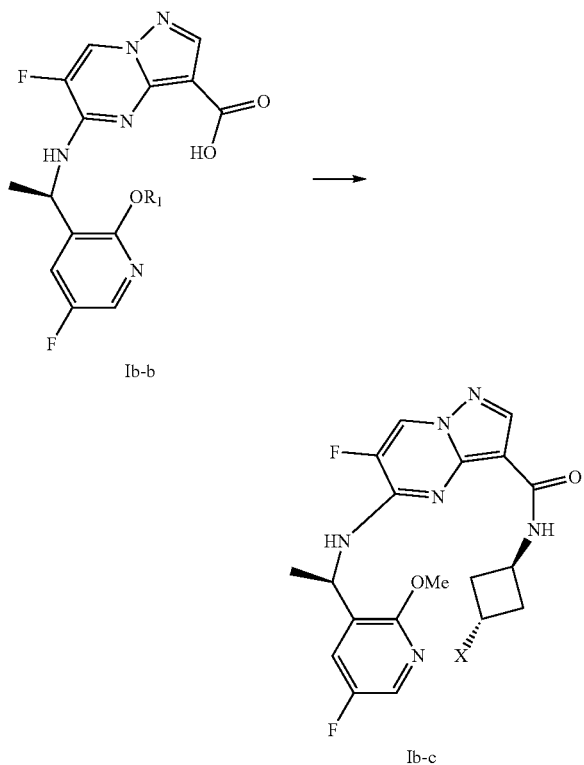

Ib-b wherein $R_1$ is $C_1$-$C_3$ alkyl, and X is halogen or

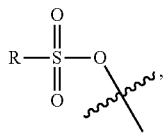

wherein R is substituted or unsubstituted $C_1$-$C_4$ alkyl and a benzene ring, and the substituted $C_1$-$C_4$ alkyl or the benzene ring is substituted by one or more (for example, one to five) substituents selected from $C_1$-$C_4$ alkyl, nitryl, halogen and methoxy; and preferably, $R_1$ is methyl or ethyl, and X is halogen or

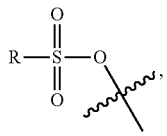

wherein R is methyl or p-tolyl.

Further, according to the preparation method of the compound of formula Ib-c of the present application, a molar mass ratio of the compound of formula Ib-b to the compound C is 1: (1 to 2); further, the molar mass ratio is 1: (1 to 1.5); and further, the molar mass ratio is 1:1.1.

Further, according to the preparation method of the compound of formula Ib-c of the present application, the reaction is carried out with alkali and a condensing agent;

further, according to the preparation method of the compound of formula Ib-c of the present application, the acid-amine condensation reaction is carried out in the presence of alkali and the condensing agent;

further, the alkali is selected from one or more of DIPEA, DMAP, TEA, N-methylmorpholine and pyridine; and further, the condensing agent is selected from one or more of CDI, HBTU, BOP, PyBOP, DCC, HOBT, EDCI and HATU.

Further, according to the preparation method of the compound of formula Ib-c of the present application, a molar mass ratio of the compound of formula Ib-b to the alkali is 1: (2 to 5); and further, the molar mass ratio is 1: (2 to 3).

Further, according to the preparation method of the compound of formula Ib-c of the present application, a molar mass ratio of the compound of formula Ib-b to the condensing agent is 1: (1 to 3); and further, the molar mass ratio is 1: (1 to 2).

Further, according to the preparation method of the compound of formula Ib-c of the present application, the acid-amine condensation reaction is carried out in a solvent; and further, according to the preparation method of the compound of formula Ib-c of the present application, the solvent is selected from one or more of DCM, DMF, toluene, THF and acetonitrile.

The present application provides a preparation method of a compound of formula Ib-d, having the following route:

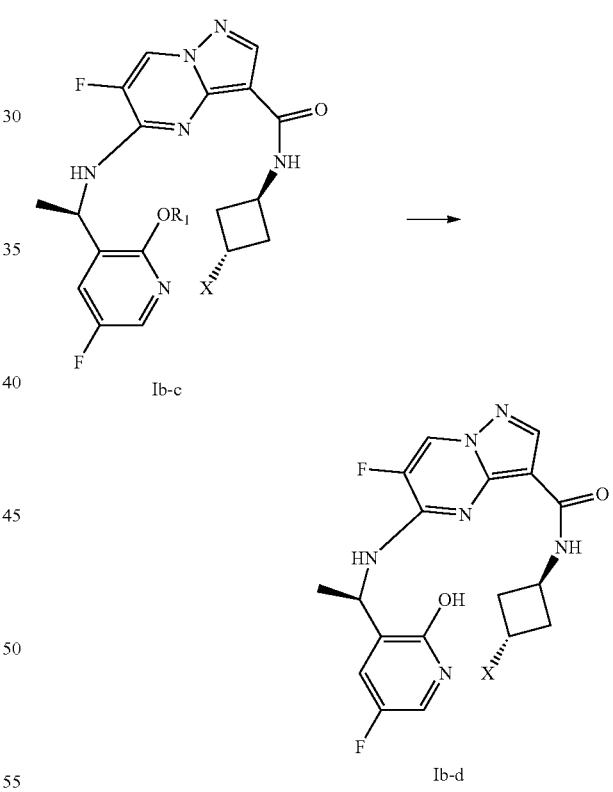

wherein $R_1$ is $C_1$-$C_3$ alkyl, and X is selected from halogen or

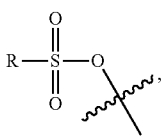

wherein R is substituted or unsubstituted $C_1$-$C_4$ alkyl or a benzene ring, and the substituted $C_1$-$C_4$ alkyl or the benzene ring is substituted by one or more (for example, one to five) substituents selected from $C_1$-$C_4$ alkyl, nitryl, halogen and methoxy; and preferably, $R_1$ is methyl or ethyl, and X is halogen or

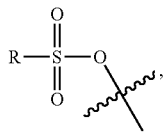

wherein R is methyl or p-tolyl.

Further, according to the preparation method of the compound of formula Ib-d of the present application, the reaction is carried out by:

mixing a compound of formula Ib-c, a solvent, a dioxane solution of HCl or an ethyl acetate solution of HCl for reaction; further, a concentration of the dioxane solution of HCl or the ethyl acetate solution of HCl ranges from 3 mol/L to 5 mol/L, and is preferably 4 mol/L; further, a volume ratio of the solvent to the dioxane solution of HCl is 1: (0.8 to 1.2), and preferably 1:1; further, a reaction temperature ranges from 50° C. to 55° C.; and further, the solvent is acetonitrile.

Further, the preparation method of the compound of formula Ib-d of the present application comprises: removing the $R_1$ substituent in the compound of formula Ib-c to obtain the compound of formula Ib-d,

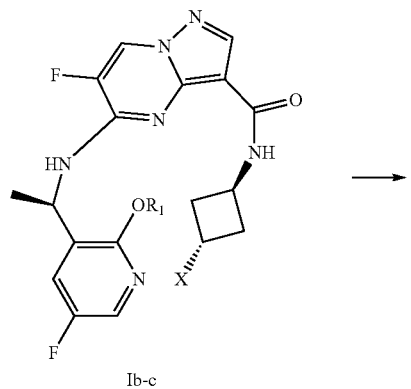

Ib-c wherein $R_1$ is $C_1$-$C_3$ alkyl, and X is halogen or

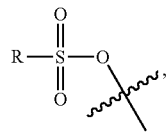

wherein R is substituted or unsubstituted $C_1$-$C_4$ alkyl or a benzene ring, and the substituted $C_1$-$C_4$ alkyl or the benzene ring is substituted by one or more (for example, one to five) substituents selected from $C_1$-$C_4$ alkyl, nitryl, halogen and methoxy; and preferably, $R_1$ is methyl or ethyl, and X is halogen or

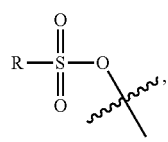

wherein R is methyl or p-tolyl.

Further, the preparation method of the compound of formula Ib-d of the present application comprises:

mixing a compound of formula Ib-c, a solvent, a dioxane solution of HCl or an ethyl acetate solution of HCl for reaction; wherein, further preferably, a concentration of the dioxane solution of HCl or the ethyl acetate solution of HCl ranges from 3 mol/L to 5 mol/L, and is preferably 4 mol/L; further preferably, a volume ratio of the solvent to the dioxane solution of HCl is 1: (0.8 to 1.2), and preferably 1:1; further preferably, a reaction temperature ranges from 50° C. to 55° C.; and further preferably, the solvent is acetonitrile.

The present application provides a preparation method of a compound of formula Ib, having the following route:

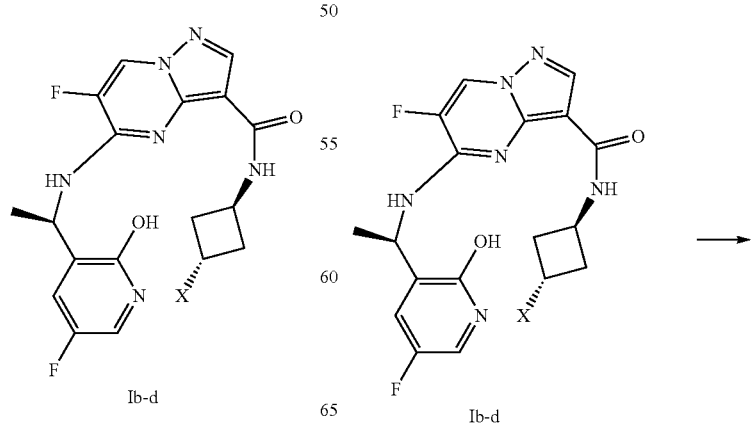

-continued

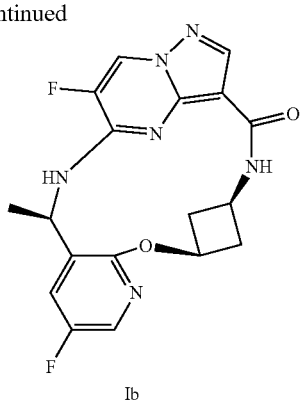

Ib wherein X is halogen or

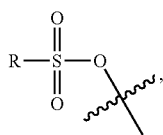

wherein R is substituted or unsubstituted $C_1$-$C_4$ alkyl or a benzene ring, and the substituted $C_1$-$C_4$ alkyl or the benzene ring is substituted by one or more (for example, one to five) substituents selected from $C_1$-$C_4$ alkyl, nitryl, halogen and methoxy; and preferably, X is halogen or

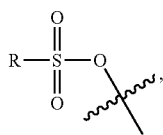

wherein R is methyl or p-tolyl.

Further, according to the preparation method of the compound of formula Ib of the present application, the reaction is carried out with alkali; further, the alkali is selected from organic alkali and/or inorganic alkali; further, the organic alkali is selected from DBU, sodium tert-butoxide, potassium tert-butoxide, sodium methoxide or sodium ethoxide, and the inorganic alkali is selected from potassium carbonate, sodium carbonate, sodium bicarbonate or cesium carbonate.

Further, according to the preparation method of the compound of formula Ib of the present application, a reaction temperature ranges from 20° C. to 50° C.; and further, the reaction temperature is 30° C.

Further, according to the preparation method of the compound of formula Ib of the present application, the reaction is carried out in a solvent, and the solvent is selected from one or more of DMF, DCM, THF, acetonitrile and toluene.

Further, the preparation method of the compound of formula Ib of the present application comprises: mixing a compound of formula Ib-d and the solvent, and then adding alkali into a reaction system in batches for reaction.

Further, according to the preparation method of the compound of formula Ib of the present application, the alkali is the inorganic alkali, and the inorganic alkali is added into the reaction system at a temperature of 5° C. to 10° C.; further, when the inorganic alkali is potassium carbonate, after the potassium carbonate is completely added, the reaction system is heated to 30° C. to 35° C. for reaction; and when the inorganic alkali is sodium bicarbonate, after the sodium bicarbonate is completely added, the reaction system is heated to 30° C. to 35° C. for reaction.

Further, the preparation method of the compound of formula Ib of the present application further comprises: preparing the compound of formula Ib-d, wherein the compound of formula Ib-d is prepared by the method described in the present application.

Further, the preparation method of the compound of formula Ib of the present application comprises: a ring-closing reaction is carried out on a compound of formula Ib-d to obtain the compound of formula Ib,

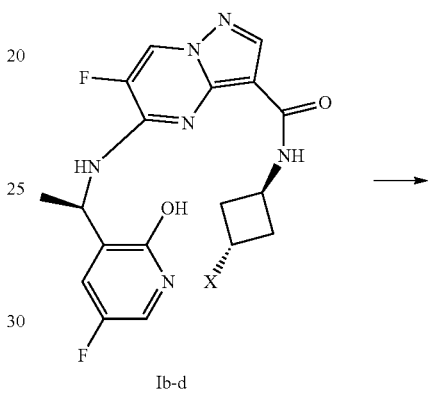

Ib-d

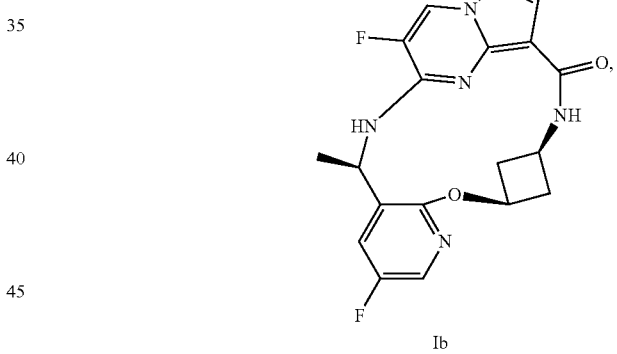

Ib wherein X is halogen or

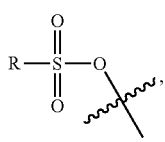

wherein R is selected from substituted or unsubstituted $C_1$-$C_4$ alkyl or a benzene ring, and the substituted $C_1$-$C_4$ alkyl or the benzene ring is substituted by one or more (for example, one to five) substituents selected from $C_1$-$C_4$ alkyl, nitryl, halogen and methoxy; and preferably, X is halogen or

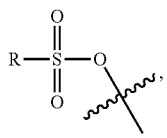

wherein R is methyl or p-tolyl.

Further, according to the preparation method of the compound of formula Ib of the present application, the ring-closing reaction is carried out in the presence of alkali; further preferably, the alkali is selected from organic alkali and/or inorganic alkali; further preferably, the organic alkali is selected from one or more of DBU, sodium tert-butoxide, potassium tert-butoxide, sodium methoxide or sodium ethoxide, and the inorganic alkali is selected from one or more of potassium carbonate, sodium carbonate, sodium bicarbonate or cesium carbonate.

Further, according to the preparation method of the compound of formula Ib of the present application, a reaction temperature of the ring-closing reaction ranges from 20° C. to 50° C.; and for example, the reaction temperature is 30° C.

Further, according to the preparation method of the compound of formula Ib of the present application, the ring-closing reaction is carried out in a solvent, and the solvent is selected from one or more of DMF, DCM, THF, acetonitrile and toluene.

Further, according to the preparation method of the compound of formula Ib of the present application, the ring-closing reaction comprises: mixing a compound of formula Ib-d and the solvent, and then adding alkali into a reaction system in batches for reaction.

Further, according to the preparation method of the compound of formula Ib of the present application, the alkali used in the ring-closing reaction is the inorganic alkali, and the inorganic alkali is added into the reaction system at a temperature of 5° C. to 10° C.; further preferably, the inorganic alkali is potassium carbonate, and after the potassium carbonate is completely added, the reaction system is heated to 30° C. to 35° C. for reaction; or the inorganic alkali is sodium bicarbonate, and after the sodium bicarbonate is completely added, the reaction system is heated to 30° C. to 35° C. for reaction.

The term "pharmaceutically acceptable" used in the present application means that a substance or a composition must be chemically and/or toxicologically compatible with other ingredients constituting a preparation and/or mammals treated with the substance or the composition.

The term "pharmaceutically acceptable salt" used in the present application comprises a conventional salt formed by a pharmaceutically acceptable inorganic or organic acid, or an inorganic or organic alkali. A preparation method of the pharmaceutically acceptable salt of the compound of the present application is known to those skilled in the art.

In the present application, the compound of the present application involved comprises the compound of formula (I), the tautomer, the mesomer, the racemate, the enantiomer, the diastereomer or the mixture thereof, or the pharmaceutically acceptable salt thereof.

The term "pharmaceutical composition" used in the present application comprises a product containing a therapeutically effective amount of the compound of the present application, and any product directly or indirectly produced by the combination of the compound of the present application. The pharmaceutical composition may be administered by a way, such as oral administration or parenteral administration. The pharmaceutical composition of the present application may be prepared into various formulations by a conventional method in the art, comprising but being not limited to a tablet, a capsule, a solution, a suspension, a granule or an injection, and may be administered by a way, such as oral administration or parenteral administration.

The term "effective amount" used in the present application means an amount sufficient to achieve a needed therapeutic effect, such as an amount capable of relieving a symptom related to a disease to be treated.

The term "treatment" used in the present application aims to relieve or eliminate a targeted disease state or illness. If a subject receives the therapeutically effective amount of the compound, the tautomer, the mesomer, the racemate, the enantiomer, the diastereomer or the mixture thereof, or the pharmaceutically acceptable salt thereof, or the pharmaceutical composition according to the method of the present application, and one or more signs and symptoms of the subject show observable and/or detectable reduction or improvement, the subject is successfully "treated". It should also be understood that the treatment of the disease state or illness comprises not only complete treatment, but also incomplete treatment, but some biological or medical related results are achieved.

In addition, it should be pointed out that a dosage and a use method of the compound of the present application depend on many factors, comprising age, weight, sex, natural health status, nutritional status, active strength of compound, administration period, metabolic rate, and severity of disease of a patient, and subjective judgment of a treating physician. Preferably, the dosage ranges from 0.001 mg/kg to 1000 mg/kg by weight per day.

According to the compound of the present application, for the same compound, if a name is inconsistent with a structural formula, the structural formula of the compound shall prevail.

BRIEF DESCRIPTION OF THE DRAWINGS

The foregoing summary, as well as the following detailed description of the preferred invention, will be better understood when read in conjunction with the appended drawing:

FIG. 1 shows $^1$H NMR data of a compound of formula Ib.

DETAILED DESCRIPTION OF THE INVENTION

In order to further illustrate the present application, a compound used as a TRK inhibitor, a preparation method thereof and an application thereof provided by the present application are described in detail hereinafter with reference to the following examples.

The following abbreviations have the following meanings:

HATU represents 2-(7-azabenzotriazol-1-yl)-N,N,N',N'-tetramethyluronium hexafluorophosphate;

HBTU represents O-benzotriazole-N,N,N',N'-tetramethyluronium-hexafluorophosphate;

DBU represents 1,8-diazabicycloundec-7-ene;

PyBOP represents benzotriazol-1-yl-oxytripyrrolidinophosphonium hexafluorophosphate;

EDCI represents 1-ethyl-3-(3-dimethylaminopropyl)carbodiimide;

$Cs_2CO_3$ represents cesium carbonate;

THF represents tetrahydrofuran;
TEA represents triethylamine;
POCl$_3$ represents phosphorus oxychloride;
DMAP represents 4-dimethylaminopyridine;
NMP represents n-methylpyrrolidone;
BOP represents a BOP reagent, which is benzotriazol-1-yloxytris(dimethylamino)-phosphonium hexafluorophosphate;
DCC represents dicyclohexylcarbodiimide;
HOBT represents 1-hydroxybenzotriazole;
SOCl$_2$ represents thionyl chloride;
(COCl)$_2$ represents oxalyl chloride;
DCM represents dichloromethane;
CDI represents N,N'-Carbonyldiimidazole;
DMF represents N,N-Dimethylformamide;
NaOH represents sodium hydroxide;
DIPEA or DIEA represents N,N-Diisopropylethylamine;
H$_2$O represents water;
TMSI represents trimethylsilyl iodide;
HCl/Dioxane represents a dioxane solution of hydrogen chloride;
rt represents a reaction temperature, which is a room temperature;
DIAD represents diisopropyl azodicarboxylate;
N,N-Diethylaniline represents N,N-Diethylaniline;
CH$_3$CN or ACN represents acetonitrile;
Zn represents zinc powder;
NH$_4$Cl represents ammonium chloride;
CH$_3$MgBr represents methylmagnesium bromide;
LiOH represents lithium hydroxide;
PPh$_3$ represents triphenylphosphine;
K$_2$CO$_3$ represents potassium carbonate;
EtOH represents ethanol;
V:V represents a volume ratio;
Pd/C represents palladium carbon;
H$_2$ represents hydrogen;
Pd(dppf)Cl$_2$ represents [1,1'-bis(diphenylphosphino)ferrocene]dichloropalladium;
XPhos represents 2-dicyclohexylphosphino-2,4,6-triisopropylbiphenyl;
OTs represents p-toluenesulfonyloxy,

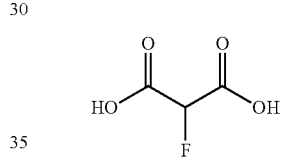

and
ee represents enantiomeric excess.

DETAILED EXAMPLES

Preparation Example 1

Preparation of ethyl 5-chloro-6-fluoropyrazo[1,5-a]pyrimidine-3-carboxylate

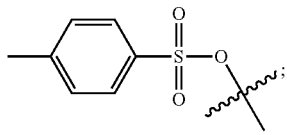 [SMILES: *OS(=O)(=O)c1ccc(C)cc1]

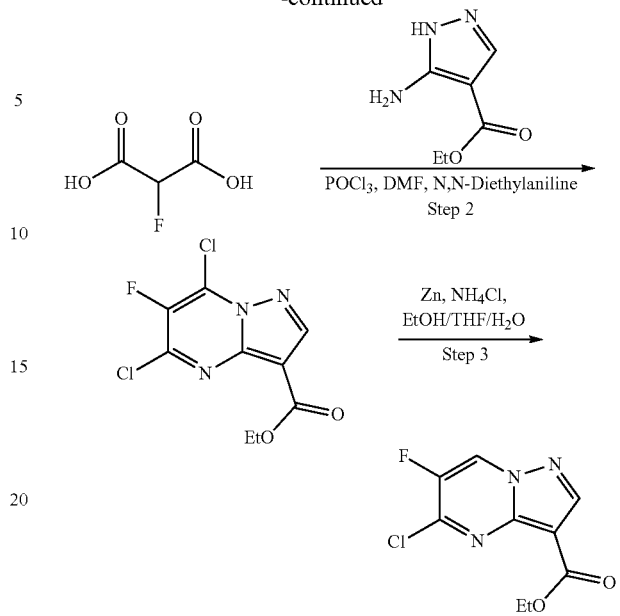

Step 1: Preparation of 2-fluoromalonic acid

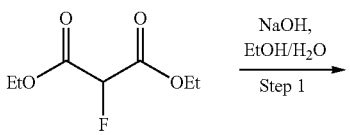

At room temperature, diethyl 2-fluoromalonate (5.0 g) and sodium hydroxide (17.3 g) were weighed and dissolved in an ethanol/water (100 mL/100 mL) mixed solution, and reacted overnight. LCMS showed that the reaction was complete. The reaction solution was concentrated to remove ethanol, and added with water (50 mL). The pH was adjusted to about 1 with concentrated hydrochloric acid. The solution was extracted with methyl tert-butyl ether for four times, and organic phases were combined, dried with anhydrous sodium sulfate, filtered and concentrated to obtain 3.7 g of the title compound, which could be used for next reaction without purification.

MS (ESI) m/z (M−H)$^+$=121.1.

Step 2: Preparation of ethyl 5,7-dichloro-6-fluoropyrazo[1,5-a]pyrimidine-3-carboxylate

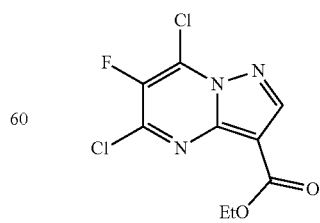

At room temperature, 2-fluoromalonic acid (2.0 g) and ethyl 5-amino-1H-pyrazole-4-carboxylate (1.7 g) were weighed and dissolved in phosphorus oxychloride (20 mL), then added with N,N-Dimethylformamide (2 mL) and N,N-Diethylaniline (4.9 g), and heated to 110° C. for reaction for 3 hours. LCMS showed that the reaction was complete. The reaction solution was concentrated to remove phosphorus oxychloride, and then poured into a saturated sodium bicarbonate solution (100 mL) to keep the solution alkaline. The solution was extracted with ethyl acetate for three times, dried with anhydrous sodium sulfate, filtered and concentrated. The obtained crude product was purified by column chromatography, and the obtained solid was washed with petroleum ether, and dried to obtain 1.7 g of the title compound.

MS (ESI) m/z (M+H)$^+$=278.0.

$^1$H NMR (400 MHz, DMSO-d$_6$) δ 8.80 (s, 1H), 4.33 (q, J=7.2 Hz, 2H), 1.32 (t, J=7.0 Hz, 3H).

Step 3: Preparation of ethyl 5-chloro-6-fluoropyrazo[1,5-a]pyrimidine-3-carboxylate

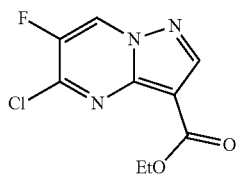 [SMILES: CCOC(=O)c1cnn2cc(F)c(Cl)nc12]

Ethyl 5,7-dichloro-6-fluoropyrazo[1,5-a]pyrimidine-3-carboxylate (1.14 g) and ammonium chloride (800 mg) were weighed and dissolved in an ethanol/tetrahydrofuran/water (30 mL/10 mL/20 mL) mixed solution, added with zinc powder (1.3 g) during stirring for reaction for 5 minutes, and then the zinc powder was filtered and removed. The filter cake was washed with ethyl acetate, the filtrate was collected, dried with anhydrous sodium sulfate, filtered and concentrated, and the obtained crude product was purified by column chromatography to obtain 800 mg of the title compound.

MS (ESI) m/z (M+H)$^+$=244.0.

$^1$H NMR (400 MHz, DMSO-d$_6$) δ 9.93 (d, J=4.4 Hz, 1H), 8.68 (s, 1H), 4.31 (q, J=7.2 Hz, 2H), 1.31 (t, J=7.2 Hz, 3H).

Preparation Example 2

Preparation of (R)-1-(5-fluoro-2-methoxypyridin-3-yl)ethyl-1-amine hydrochloride

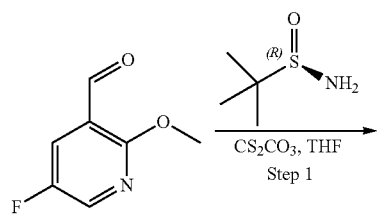

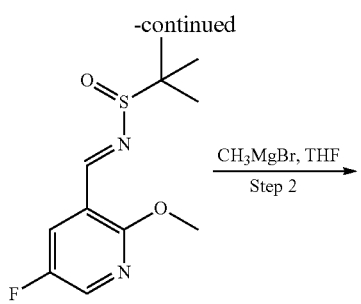

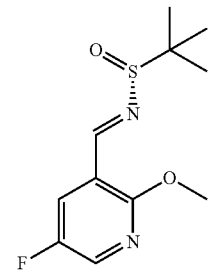 [SMILES: COc1ncc(F)cc1/C=N/[S@](=O)C(C)(C)C]

Step 1: Preparation of (R)—N-(((5-fluoro-2-methoxypyridin-3-yl)methylene)-2-methylpropane-2-sulfenamide (R)-2-methylpropane-2-sulfenamide (12.9 g) was dissolved in tetrahydrofuran (100 mL), and then added with 5-fluoro-2-methoxynicotinaldehyde (15.0 g) and cesium carbonate (40.9 g) in sequence. The obtained mixture reacted at room temperature for 2 hours. TLC showed that raw materials were completely consumed. The reaction solution was subjected to suction filtration, the filter cake was washed with tetrahydrofuran for three times, and the obtained filtrate was washed with a saturated sodium chloride solution once, dried with anhydrous sodium sulfate, filtered and concentrated. The obtained crude product was purified by column chromatography to obtain 23.0 g of the title compound.

MS (ESI) m/z (M+H)$^+$=259.1.

$^1$H NMR (400 MHz, DMSO-d$_6$) δ 8.67 (d, J=2.4 Hz, 1H), 8.42 (d, J=3.2 Hz, 1H), 8.14 (dd, J=8.4, 3.2 Hz, 1H), 3.98 (s, 3H), 1.18 (s, 9H).

Step 2: Preparation of (R)—N—((R)-1-(5-fluoro-2-methoxypyridin-3-yl)ethyl)-2-methylpropane-2-sulfenamide

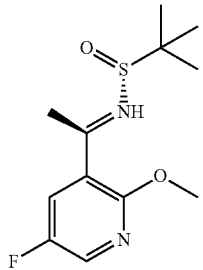

(R)—N-(((5-fluoro-2-methoxypyridin-3-yl)methylene)-2-methylpropane-2-sulfenamide (5.0 g) was weighed and dissolved in tetrahydrofuran (40 mL). The obtained mixture was cooled to −78° C., and dropwise added with methylmagnesium bromide (7.8 mL, 3 M) slowly, and the temperature was kept below −65° C. After the dropwise addition was complete, the temperature was recovered to room temperature naturally, and the reaction was continued for 1 hour. TLC showed that the reaction was complete. The reaction solution was poured into a saturated ammonium chloride solution (1 L), and extracted with ethyl acetate, and organic phases were combined, washed with a saturated sodium chloride solution, dried with anhydrous sodium sulfate, filtered and concentrated. The obtained crude product was purified by column chromatography to obtain 4.5 g of the title compound.

MS (ESI) m/z (M+H)$^+$=275.2.

$^1$H NMR (400 MHz, DMSO-d$_6$) δ 8.04 (d, J=2.8 Hz, 1H), 7.74 (dd, J=9.2, 3.2 Hz, 1H), 5.80 (d, J=8.8 Hz, 1H), 4.57-4.50 (m, 1H), 3.88 (s, 3H), 1.33 (d, J=6.8 Hz, 3H), 1.11 (s, 9H).

Step 3: Preparation of (R)-1-(5-fluoro-2-methoxypyridin-3-yl)ethyl-1-amine hydrochloride

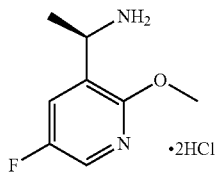

At room temperature, (R)—N—((R)-1-(5-fluoro-2-methoxypyridin-3-yl)ethyl)-2-methylpropane-2-sulfenamide (4.5 g) was dissolved in a 1,4-dioxane solution of hydrogen chloride (4 M, 30 mL), and reacted overnight. LCMS showed that raw materials were completely consumed. The reaction solution was concentrated to obtain 3.1 g of crude product, wherein ee was higher than 95%, and the crude product could be directly used in the next step without purification.

MS (ESI) m/z (M+H)$^+$=171.2.

$^1$H NMR (400 MHz, DMSO-d$_6$) δ 8.80-8.66 (m, 3H), 8.18 (d, J=2.8 Hz, 1H), 8.04-8.00 (m, 1H), 7.09-6.60 (m, 1H), 4.51-4.45 (m, 1H), 3.90 (s, 3H), 1.49 (d, J=6.4 Hz, 3H).

Preparation Example 3

Preparation of (R)-5-fluoro-3-(1-(2,2,2-trifluoroacetyl)pyrrolidin-2-yl)pyridin-2-yl trifluoromethanesulfonate

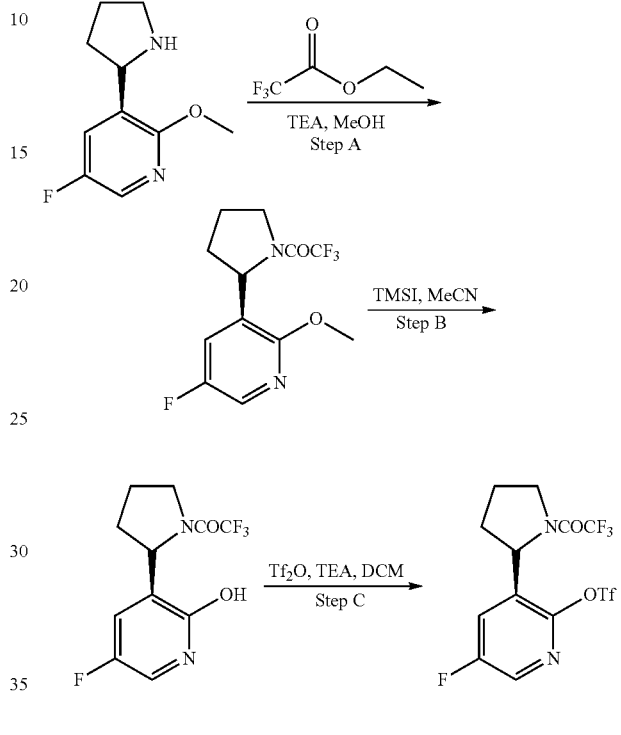

Step A: Preparation of (R)-2,2,2-trifluoro-1-(2-(5-fluoro-2-methoxypyridin-3-yl)pyrrolidin-1-yl)ethyl-1-one

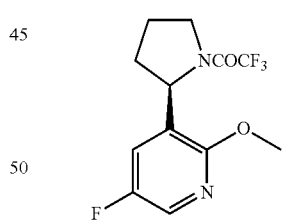

(R)-5-fluoro-2-methoxy-3-(pyrrolidin-2-yl)pyridine (2.6 g) was weighed and dissolved in methanol (25 mL), added with triethylamine (2.0 g), and added with ethyl trifluoroacetate (2.8 g) at 0° C. After the addition was complete, the obtained mixture reacted at room temperature overnight. After LCMS showed that the reaction was complete, the reaction solution was poured into 20 mL of water, and extracted with ethyl acetate, and organic phases were combined, washed with saturated saline once, dried with anhydrous sodium sulfate, then filtered and concentrated. The obtained crude product was purified by column chromatography to obtain 2.0 g of the title compound.

MS (ESI) m/z (M+H)$^+$=293.1

Step B: Preparation of (R)-2,2,2-trifluoro-1-(2-(5-fluoro-2-methoxypyridin-3-yl)pyrrolidin-1-yl)ethyl-1-one

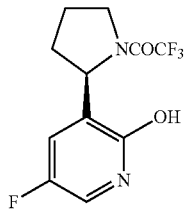

(R)-2,2,2-trifluoro-1-(2-(5-fluoro-2-methoxypyridin-3-yl)pyrrolidin-1-yl)ethyl-1-one (2.0 g) was weighed and dissolved in acetonitrile (20 mL), and dropwise added with iodotrimethylsilane (14.0 g) at room temperature, and reacted at room temperature overnight after the addition was complete. After the reaction was complete, the reaction solution was poured into 1 M sodium thiosulfate solution (30 mL), and extracted with dichloromethane, and organic phases were combined, washed with a saturated saline solution once, dried with anhydrous sodium sulfate, filtered and concentrated. The obtained crude product was purified by column chromatography to obtain 1.7 g of the title compound.

MS (ESI) m/z (M+H)$^+$=279.1

Step C: Preparation of (R)-5-fluoro-3-(1-(2,2,2-trifluoroacetyl)pyrrolidin-2-yl)pyridin-2-yl trifluoromethanesulfonate

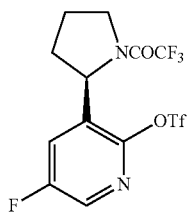

(R)-2,2,2-trifluoro-1-(2-(5-fluoro-2-methoxypyridin-3-yl)pyrrolidin-1-yl)ethyl-1-one (1.2 g) was weighed and dissolved in dichloromethane (12 mL), added with triethylamine (1.0 g), and dropwise added with trifluoromethanesulfonic anhydride (2.2 g) slowly, and reacted at room temperature overnight after the addition was complete. After TLC showed that the reaction was complete, the reaction solution was poured into water (20 mL), and extracted with dichloromethane, and organic phases were combined, washed with a saturated saline solution once, dried with anhydrous sodium sulfate, filtered and concentrated. The obtained crude product was purified by column chromatography to obtain 1.5 g of the title compound.

MS (ESI) m/z (M+H)$^+$=411.1

Preparation Example 4

Preparation of (R)-1-(2-methoxypyridin-3-yl)ethyl-1-amine hydrochloride

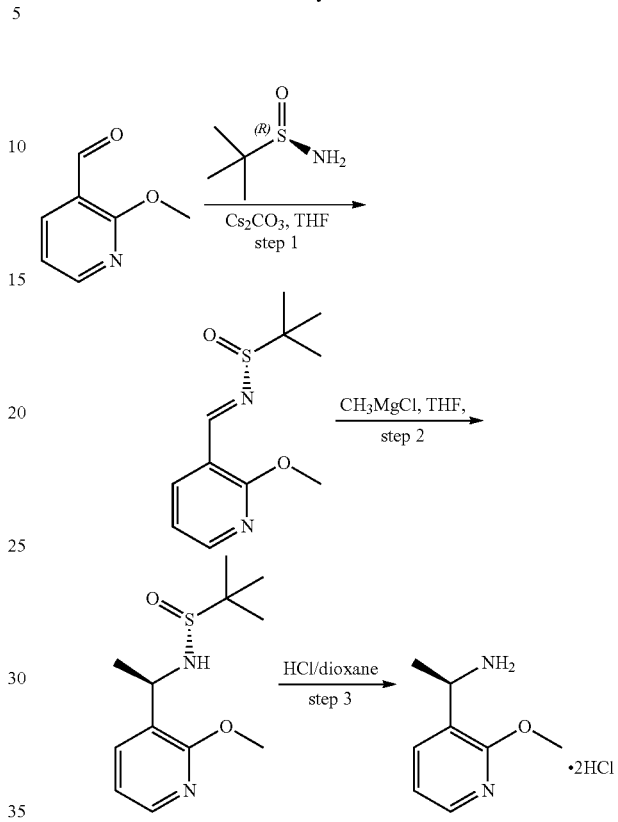

Step 1: Preparation of (R, E)-N-((2-methoxypyridin-3-yl)methylene)-2-methylpropane-2-sulfenamide

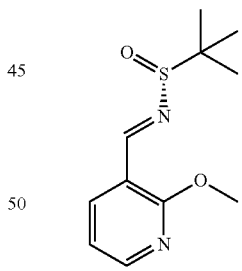

(R)-2-methylpropane-2-sulfenamide (4.2 g) was dissolved in tetrahydrofuran (50 mL), and then added with 2-methoxynicotinaldehyde (4.0 g) and cesium carbonate (14.2 g) in sequence. The obtained mixture reacted at room temperature for 2 hours. TLC showed that raw materials were completely consumed. The reaction solution was subjected to suction filtration, the filter cake was washed with tetrahydrofuran for three times, and the obtained filtrate was washed with a saturated sodium chloride solution once, dried with anhydrous sodium sulfate, filtered and concentrated. The obtained crude product was purified by column chromatography to obtain 6.1 g of the title compound.

MS (ESI) m/z (M+H)$^+$=241.1

Step 2: Preparation of (R)—N—((R)-1-(2-methoxypyridin-3-yl)ethyl)-2-methylpropane-2-sulfenamide

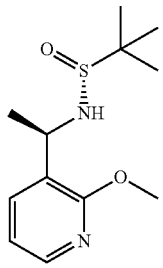 [SMILES: COc1ncccc1[C@@H](C)N[S@](=O)C(C)(C)C]

(R,E)-N-((2-methoxypyridin-3-yl)methylene)-2-methylpropane-2-sulfenamide (6.1 g) was dissolved in tetrahydrofuran (60 mL). The obtained mixture was cooled to −78° C., and then dropwise added with methylmagnesium chloride (11.0 mL, 3 M) slowly, and the temperature was kept below −65° C. during dropwise adding. After the dropwise addition was complete, the temperature was recovered to room temperature naturally, and the reaction was continued for 1 hour. The reaction solution was poured into a saturated ammonium chloride solution (1 L), and extracted with ethyl acetate, and organic phases were washed with a saturated sodium chloride solution once, dried with anhydrous sodium sulfate, filtered and concentrated. The obtained crude product was purified by column chromatography and then pulped with petroleum ether to obtain 1.0 g of the title compound.
MS (ESI) m/z (M+H)$^+$=257.2

Step 3: Preparation of (R)-1-(2-methoxypyridin-3-yl)ethyl-1-amine hydrochloride

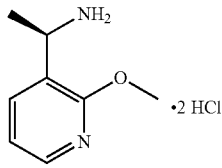

(R)—N—((R)-1-(2-methoxypyridin-3-yl)ethyl)-2-methylpropane-2-sulfenamide (1.0 g) was dissolved in dioxane hydrochloride (20 mL), and the system reacted at room temperature overnight. LCMS showed that raw materials were completely consumed. The system was concentrated, and the obtained crude product (840 mg) could be directly used in the next step.
MS (ESI) m/z (M+H)$^+$=153.2

Preparation Example 5

Preparation of 5-chloro-2-fluoropyrazo[1,5-a]pyrimidine-3-carboxylic acid

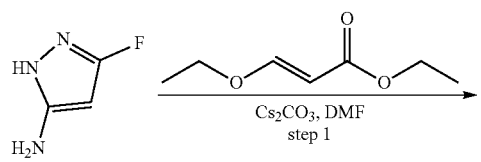

Step 1: Preparation of 2-fluoropyrazo[1,5-c]pyrimidine-5-ol

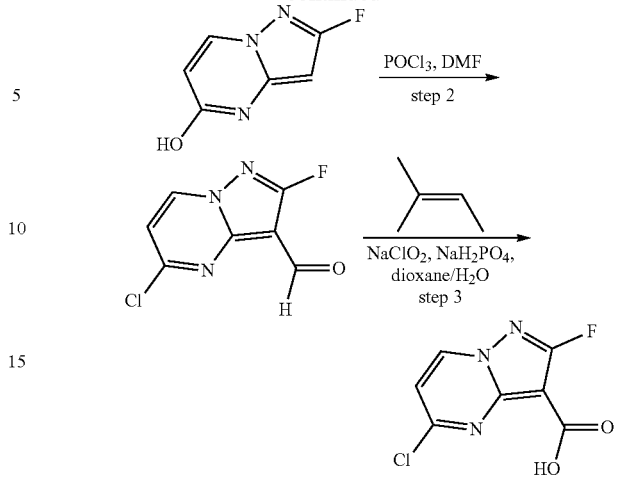

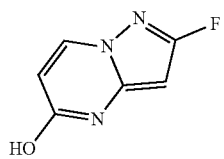 [SMILES: Oc1ccn2nc(F)cc2n1]

3-fluoro-1H-pyrazole-5-amine (2.1 g) and (E)-ethyl 3-ethoxyacrylate (4.5 g) was dissolved in N,N-Dimethylacetamide (50 mL), and then added with cesium carbonate (20.3 g). The obtained mixture reacted at 100° C. overnight. TLC showed that raw materials were completely consumed. The reaction solution was poured into 100 mL of water, and extracted with ethyl acetate for three times, organic phases were combined, washed with a saturated sodium chloride solution, dried with anhydrous sodium sulfate, filtered and concentrated. The obtained crude product was purified by column chromatography to obtain 2.7 g of the title compound.
MS (ESI) m/z (M+H)$^+$=154.2

Step 2: Preparation of 5-chloro-2-fluoropyrazo[1,5-c]pyrimidine-3-formaldehyde

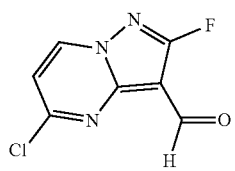 [SMILES: O=Cc1c(F)nn2ccc(Cl)nc12]

2-fluoropyrazo[1,5-a]pyrimidine-5-ol (2.7 g) was dissolved in N,N-Dimethylacetamide (50 mL), and then added with phosphorus oxychloride (13.5 g). The obtained mixture reacted at 100° C. for 3 hours. TLC showed that raw materials were completely consumed. The reaction solution was poured into 50 mL of water for quenching, and extracted with ethyl acetate for three times, and organic phases were combined, washed with a saturated sodium chloride solution, dried with anhydrous sodium sulfate, filtered and concentrated. The obtained crude product was purified by column chromatography to obtain 3.3 g of the title compound.

MS (ESI) m/z (M+H)$^+$=200.1

Step 3: Preparation of 5-chloro-2-fluoropyrazo[1,5-c]pyrimidine-3-carboxylic acid

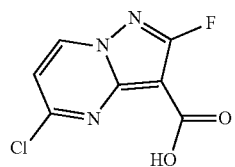 [SMILES: O=C(O)c1c(F)nn2ccc(Cl)nc12]

Sodium chlorite (4.5 g) and sodium dihydrogen phosphate (3.0 g) were dissolved in water (15 mL), and slowly added into a dioxane (40 mL) solution of 5-chloro-2-fluoropyrazo[1,5-a]pyrimidine-3-formaldehyde (1.0 g) and 2-methyl-2-butene (9 mL) at 0° C. After the addition was complete, the obtained mixture reacted at room temperature for 5 hours. TLC showed that raw materials were completely consumed. The reaction solution was poured into 100 mL of water, and extracted with ethyl acetate for three times, and organic phases were combined, washed with a saturated sodium chloride solution, dried with anhydrous sodium sulfate, filtered and concentrated. The obtained crude product was purified by column chromatography to obtain 521 mg of the title compound.

MS (ESI) m/z (M+H)$^+$=216.2

Example 1

Preparation of (1$^3$E,1$^4$E,2$^2$R,6R)-1$^6$,3$^5$-difluoro-6-methyl-7-aza-1(5,3)-pyrazolo[1,5-a]pyrimidine-3(3,2)-pyrazolo-2(1,2)-pyrrolidinyl cyclooctane-8-one

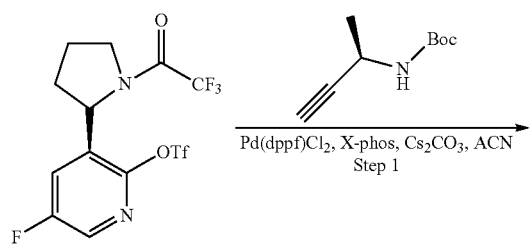

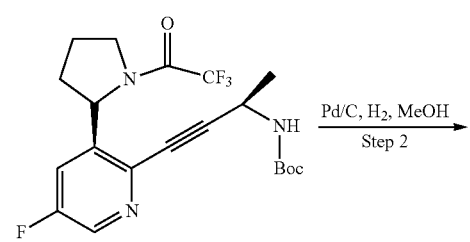

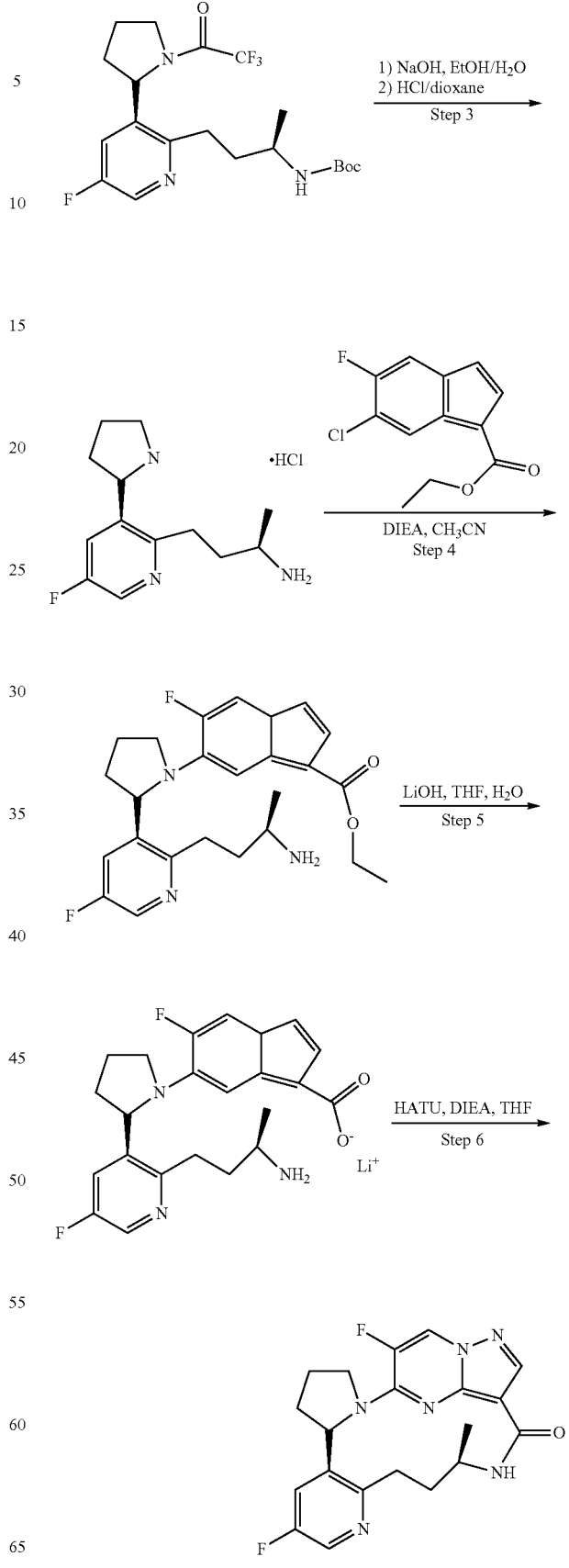

Step 1: Preparation of tert-butyl(R)-4-(5-fluoro-3-((R)-1-(2,2,2-trifluoroacetyl)pyrrolidin-2-yl)pyridin-2-yl)but-3-yn-2-yl carbamate

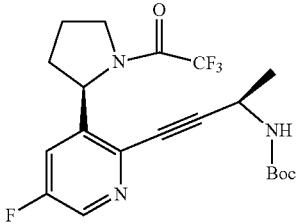 [SMILES: C[C@H](C#Cc1ncc(F)cc1[C@H]1CCCN1C(=O)C(F)(F)F)NC(=O)OC(C)(C)C]

In argon atmosphere, (R)-5-fluoro-3-(1-(2,2,2-trifluoroacetyl)pyrrolidin-2-yl)pyridin-2-yl trifluoromethane sulfonate (2.68 g) was dissolved in acetonitrile (25 mL), and added with (R)-tert-butyl but-3-alkyn-2-yl carbamate (1.6 g), [1,1'-bis(diphenylphosphino)ferrocene]palladium dichloride (0.5 g), 2-dicyclohexyl phosphorus-2,4,6-triisopropyl biphenyl (0.6 g) and cesium carbonate (6.3 g) in sequence. The obtained mixture was heated to 80° C. for reaction for 2 hours. TLC showed that the reaction was complete. The reaction solution was cooled to room temperature and filtered, the filtrate was concentrated, and the obtained crude product was purified by column chromatography to obtain 1.9 g of the title compound.

MS (ESI) m/z (M+H)$^+$=430.2.

Step 2: Preparation of tert-butyl(R)-4-(5-fluoro-3-((R)-1-(2,2,2-trifluoroacetyl)pyrrolidin-2-yl)pyridin-2-yl)butyl-2-yl)carbamate

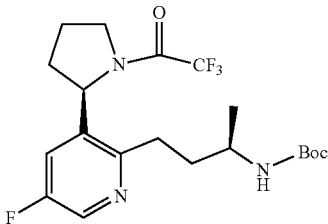 [SMILES: C[C@H](CCc1ncc(F)cc1[C@H]1CCCN1C(=O)C(F)(F)F)NC(=O)OC(C)(C)C]

In hydrogen atmosphere, tert-butyl(R)-4-(5-fluoro-3-((R)-1-(2,2,2-trifluoroacetyl)pyrrolidin-2-yl)pyridin-2-yl)but-3-yn-2-yl carbamate (1.6 g) was dissolved in anhydrous methanol (15 mL), and added with palladium/carbon (160 mg, 10% w/w). The obtained mixture reacted at room temperature for 4 hours. TLC showed that the reaction was complete. The reaction solution was filtered, the filtrate was concentrated, and the obtained crude product was purified by column chromatography to obtain 1.1 g of the title compound.

MS (ESI) m/z (M+H)$^+$=434.2.

Step 3: Preparation of (R)-4-(5-fluoro-3-((R)-pyrrolidin-2-yl)pyridin-2-yl)but-2-amine hydrochloride

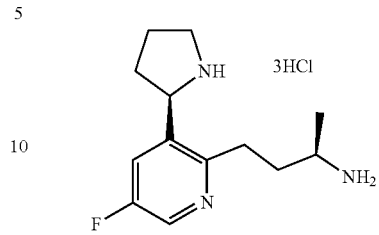

Tert-butyl(R)-4-(5-fluoro-3-((R)-1-(2,2,2-trifluoroacetyl)pyrrolidin-2-yl)pyridin-2-yl)butyl-2-yl)carbamate (600 mg) was dissolved in anhydrous ethanol (5 mL), and added with a sodium hydroxide solution (2 M, 3 mL). The obtained mixture was heated to 60° C. for reaction for 2 hours. TLC showed that the reaction was complete. The reaction solution was cooled to room temperature, added with a 1,4-dioxane solution of hydrogen chloride (4 M, 7 mL), and continuously stirred at room temperature until the reaction was complete. The system was directly concentrated to obtain 2.1 g of crude product, which could be directly used for next reaction without purification.

MS (ESI) m/z (M+H)$^+$=238.1.

Step 4: Preparation of ethyl 5-((R)-2-(2-(R)-3-aminobutyl)-5-fluoropyridin-3-yl)-pyrrol-1-yl)-6-fluoropyrazo[1,5-c]pyrimidine-3-carboxylate

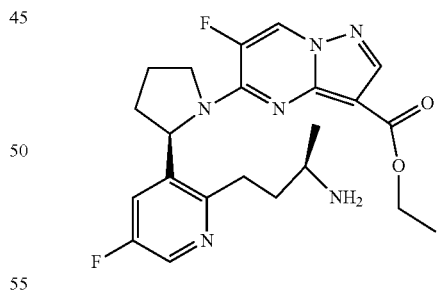

At room temperature, (R)-4-(5-fluoro-3-((R)-pyrrolidin-2-yl)pyridin-2-yl)but-2-amine hydrochloride (2.1 g) was dissolved in acetonitrile (10 mL), ethyl 5-chloro-6-fluoropyrazo[1,5-c]pyrimidine-3-carboxylate (369 mg) and N,N-Diisopropylethylamine (1.6 g) were added in sequence, and an obtained mixture was heated to 60° C. for reaction. After the reaction was complete, the reaction solution was filtered, the filtrate was concentrated, and the obtained crude product was purified by column chromatography to obtain 1.6 g of the title compound.

MS (ESI) m/z (M+H)$^+$=445.2.

Step 5: Preparation of 5-((R)-2-(2-(R)-3-aminobutyl)-5-fluoropyridin-3-yl)-pyrrol-1-yl)-6-fluoropyrazo[1,5-c]pyrimidine-3-carboxylic acid lithium salt

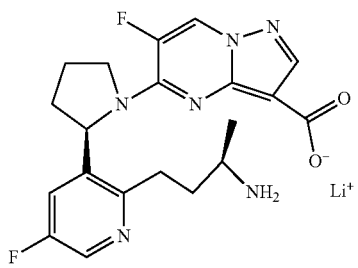 [SMILES: C[C@@H](N)CCc1ncc(F)cc1[C@H]1CCCN1c1nc2c(C(=O)[O-])cnn2cc1F ; [Li+]]

At room temperature, ethyl 5-((R)-2-(2-((R)-3-aminobutyl)-5-fluoropyridin-3-yl)-pyrrol-1-yl)-6-fluoropyrazo[1,5-c]pyrimidine-3-carboxylate (400 mg) was dissolved in tetrahydrofuran (5 mL), and added with a lithium hydroxide solution (2 M, 2.7 mL). The obtained mixture was heated to 55° C. for reaction. After the reaction was complete, the reaction solution was concentrated to remove tetrahydrofuran, and freeze-dried to obtain 390 mg of crude product, which could be directly used for next reaction without purification.

MS (ESI) m/z (M+H)$^+$=417.2.

Step 6: Preparation of (1$^3$E,1$^4$E,2$^2$R,6R)-1$^6$,3$^5$-difluoro-6-methyl-7-aza-1(5,3)-pyrazolo[1,5-c]pyrimidine-3(3,2)-pyrazolo-2(1,2)-pyrrolidinyl cyclooctane-8-one

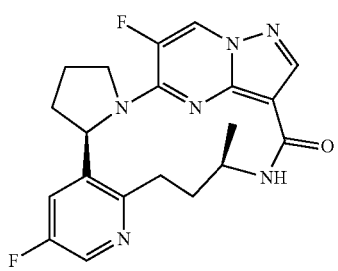 [SMILES: C[C@@H]1CCc2ncc(F)cc2[C@H]2CCCN2c2nc3c(cnn3cc2F)C(=O)N1]

At room temperature, 5-((R)-2-(2-((R)-3-aminobutyl)-5-fluoropyridin-3-yl)-pyrrol-1-yl)-6-fluoropyrazo[1,5-c]pyrimidine-3-carboxylic acid lithium salt (340 mg) was dissolved in tetrahydrofuran (25 mL), added with 2-(7-benzotriazole oxide)-N,N,N',N'-tetramethylurea hexafluorophosphate (800 mg) and N,N-Diisopropylethylamine (782 mg) in sequence, and stirred for reaction for 3 hours. TLC showed that the reaction was complete. The reaction solution was directly filtered, the solid was washed with ethyl acetate, the filtrate was concentrated to obtain 1.2 g of crude product, and the crude product was purified by column chromatography to obtain 9 mg of the title compound, wherein ee value was higher than 99%.

MS (ESI) m/z (M+H)$^+$=399.2.
$^1$H NMR (400 MHz, DMSO-d$_6$) δ 9.20 (d, J=8.0 Hz, 1H), 8.37 (d, J=4.0 Hz, 1H), 8.13 (d, J=8.0 Hz, 1H), 8.05 (s, 1H), 7.59 (dd, J=8.0, 4.0 Hz, 1H), 5.59 (t, J=8.0 Hz, 1H), 4.29-4.23 (m, 1H), 4.20-4.10 (m, 1H), 4.07-4.03 (m, 1H), 2.86-2.68 (m, 3H), 2.49-2.43 (m, 1H), 2.23-2.18 (m, 1H), 2.10-1.99 (m, 2H), 1.76-1.69 (m, 1H), 1.21 (d, J=4.0 Hz, 3H).

Example 2

Preparation of ((1$^3$E,1$^4$E,2$^2$R,5$^1$S,5$^3$S)-1$^6$,3$^5$-difluoro-4-oxa-6-aza-1(5,3)-pyrazolo[1,5-a]pyrimidine-3(3,2)-pyridine-2(1,2)-pyrrolidine-5(1,3)-cyclobutancycloheptan-7-one

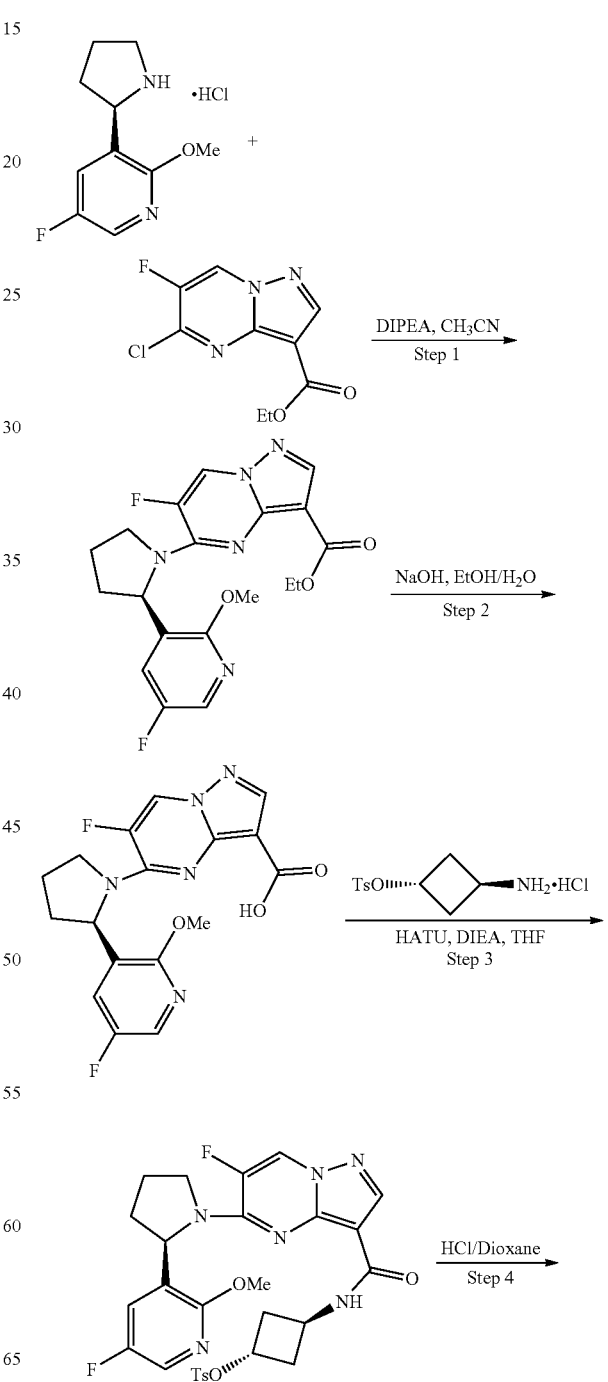

-continued

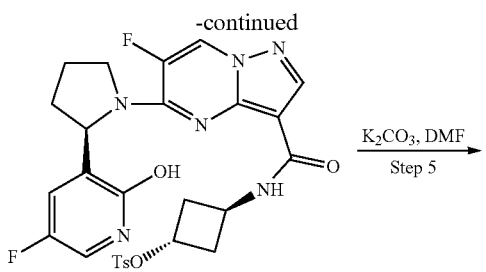

K₂CO₃, DMF
Step 5

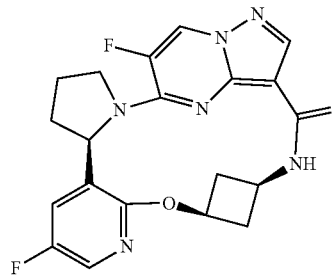

Step 1: Preparation of ethyl (R)-6-fluoro-5-(2-(5-fluoro-2-methoxypyridin-3-yl)pyrrolidin-1-yl)pyrazolo[1,5-c]pyrimidine-3-carboxylate

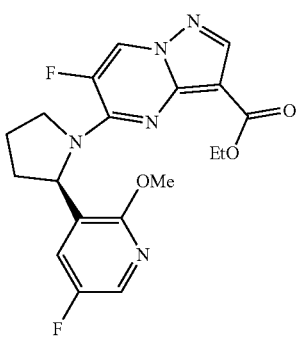 [SMILES: COc1ncc(F)cc1[C@H]1CCCN1c1nc2c(C(=O)O)cnn2cc1F]

(R)-5-fluoro-2-methoxy-3-(pyrrolidin-2-yl)pyridine hydrochloride (334 mg) was dissolved in acetonitrile (10 mL), and then added with N,N-Diisopropylethylamine (789 mg) and ethyl 5-chloro-6-fluoropyrazo[1,5-c]pyrimidine-3-carboxylate (350 mg) in sequence. The obtained mixture reacted at 60° C. for 3 hours. TLC showed that the reaction was complete. The reaction solution was poured into water (50 mL), and extracted with dichloromethane, and organic phases were combined, washed with a saturated sodium chloride solution, dried with anhydrous sodium sulfate, filtered and concentrated. The obtained crude product was purified by column chromatography to obtain 570 mg of the title compound.

MS (ESI) m/z (M+H)⁺=404.2.

Step 2: Preparation of (R)-6-fluoro-5-(2-(5-fluoro-2-methoxypyridin-3-yl)pyrrolidin-1-yl)pyrazolo[1,5-a]pyrimidine-3-carboxylic acid

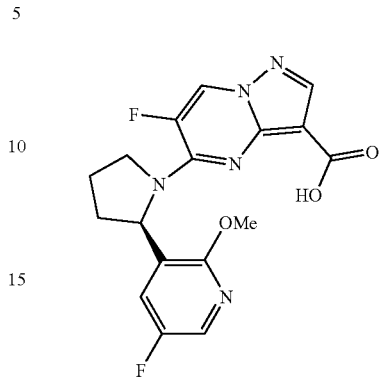

Ethyl (R)-6-fluoro-5-(2-(5-fluoro-2-methoxypyridin-3-yl)pyrrolidin-1-yl)pyrazolo[1,5-c]pyrimidine-3-carboxylate (570 mg) was dissolved in an ethanol/water (5 mL/15 mL) mixed solution, and then added with sodium hydroxide (282 mg). The obtained mixture reacted at 50° C. overnight. TLC showed that the reaction was complete. The reaction solution was poured into water (30 mL), The pH was adjusted to about 5 with a hydrogen chloride solution (2 M). The solution was extracted with dichloromethane, and organic phases were combined, washed with a saturated sodium chloride solution, dried with anhydrous sodium sulfate, filtered and concentrated to obtain 450 mg of the title compound, which could be directly used in the next step without purification.

MS (ESI) m/z (M+H)⁺=376.2.

Step 3: Preparation of cyclobutyl ((1R,3r)-3-(6-fluoro-5-((R)-2-(5-fluoro-2-methoxypyridin-3-yl)pyrrolidin-1-yl)pyrazolo[1,5-c]pyrimidine-3-carboxamido)-4-methylbenzenesulfonate

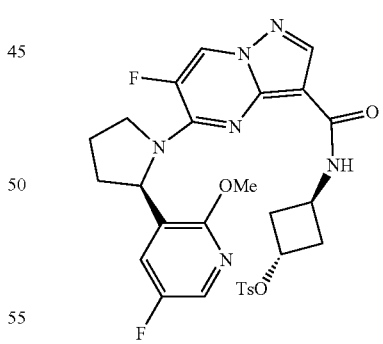

(R)-6-fluoro-5-(2-(5-fluoro-2-methoxypyridin-3-yl)pyrrolidin-1-yl)pyrazolo[1,5-c]pyrimidine-3-carboxylic acid (300 mg), 2-(7-azobenzotriazole)-N,N,N',N'-tetramethyl-urea hexafluorophosphate (456 mg) and N,N-Diisopropylethylamine (258 mg) were dissolved in dried tetrahydrofuran (10 mL) for reaction at room temperature for 1 hour, and then added with tert-butyl (3-hydroxycyclobutyl)carbamate hydrochloride (231 mg) for continuous reaction for 1 hour. TLC showed that the reaction was complete. The reaction solution was poured into water (30 mL), and extracted with ethyl acetate, and organic phases were combined, washed with a saturated sodium chloride solution, dried with anhydrous sodium sulfate, filtered and concentrated. The obtained crude product was purified by column chromatography to obtain 350 mg of the title compound.
MS (ESI) m/z (M+H)+=599.2.

Step 4: Preparation of cyclobutyl ((1R,3R)-3-(6-fluoro-5-((R)-2-(5-fluoro-2-hydroxypyridin-3-yl)pyrrolidin-1-yl)pyrazolo[1,5-c]pyrimidine-3-carboxamido)-4-methylbenzenesulfonate

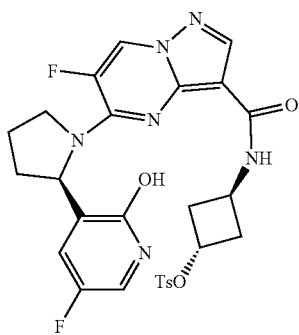 [SMILES: Cc1ccc(S(=O)(=O)O[C@H]2C[C@H](NC(=O)c3cnn4cc(F)c(N5CCC[C@@H]5c5cc(F)cnc5O)nc34)C2)cc1]

Cyclobutyl ((1R,3R)-3-(6-fluoro-5-((R)-2-(5-fluoro-2-methoxypyridin-3-yl)pyrrolidin-1-yl)pyrazolo[1,5-c]pyrimidine-3-carboxamido)-4-methylbenzenesulfonate (300 mg) was weighed and added into 1,4-dioxane of hydrogen chloride (4 M, 10 mL). The obtained mixture reacted at 55° C. overnight. TLC showed that the reaction was complete. The reaction solution was concentrated to remove most of the 1,4-dioxane to obtain 300 mg of crude product, which could be directly used in the next step without purification.
MS (ESI) m/z (M+H)+=585.2.

Step 5: Preparation of ((1³E,1⁴E,2²R,5¹S,5³S)-1⁶,3⁵-difluoro-4-oxa-6-aza-1(5,3)-pyrazolo[1,5-c]pyrimidine-3(3,2)-pyridine-2(1,2)-pyrrolidine-5(1,3)-cyclobutancycloheptan-7-one

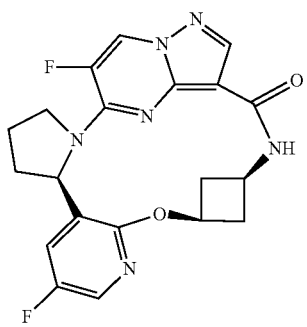 [SMILES: O=C1N[C@H]2C[C@H](C2)Oc2ncc(F)cc2[C@H]2CCCN2c2nc3c1cnn3cc2F]

Cyclobutyl ((1R,3R)-3-(6-fluoro-5-((R)-2-(5-fluoro-2-hydroxypyridin-3-yl)pyrrolidin-1-yl)pyrazolo[1,5-c]pyrimidine-3-carboxamido)4-methylbenzenesulfonate (150 mg) was dissolved in N,N-Dimethylformamide (6 mL), and then added with potassium carbonate (116 mg). The obtained mixture reacted at room temperature for 5 hours. TLC showed that the reaction was complete. The reaction solution was purified by a preparative high performance liquid chromatography (HPLC) to obtain 44 mg of the title compound, wherein ee value was higher than 99%.
MS (ESI) m/z (M+H)+=413.2.
¹H NMR (400 MHz, d₆-DMSO) δ 9.23 (1H, d, J=8.0 Hz), 8.73 (1H, d, J=10.4 Hz), 8.13 (1H, s), 8.03 (1H, d, J=3.2 Hz), 7.80 (1H, dd, J=10.0, 4.0 Hz), 5.93-5.90 (1H, m), 5.14-5.11 (1H, m), 4.69-4.65 (1H, m), 4.38-4.34 (1H, m), 3.95-3.91 (1H, m), 3.09-3.02 (1H, m), 2.88-2.84 (1H, m), 2.38-2.27 (2H, m), 2.16-2.06 (2H, m), 1.77-1.66 (2H, m).

Example 3

Preparation of (3¹S,3³S,6³E,6⁴E,8R)-1⁵,6⁶-difluoro-8-methyl-2-oxo-4,7-diaza-6(3,5)-pyrazolo[1,5-a]pyrimidine-1(2,3)-pyridine-3(1,3)-cyclobutylcyclooctane-5-one (Compound Ib)

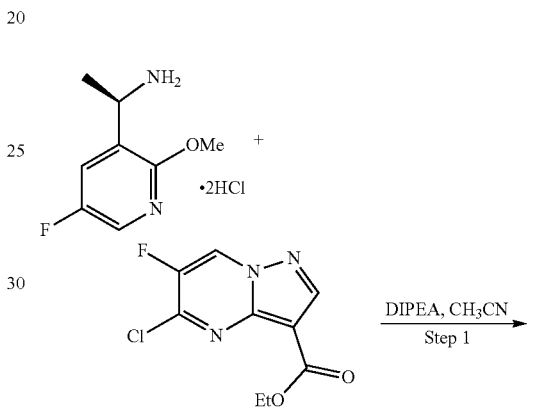

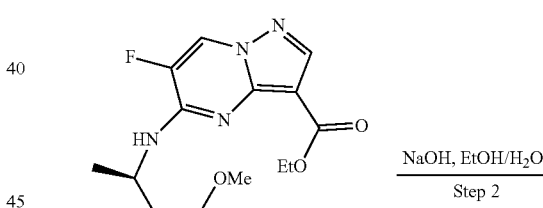

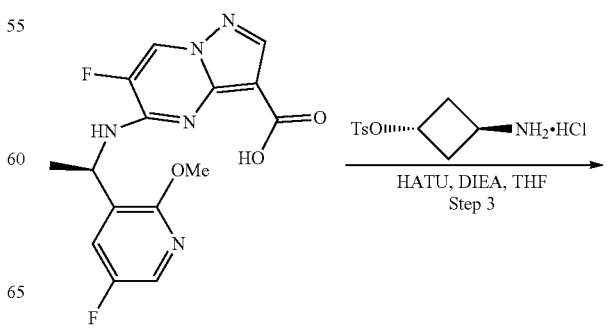

-continued

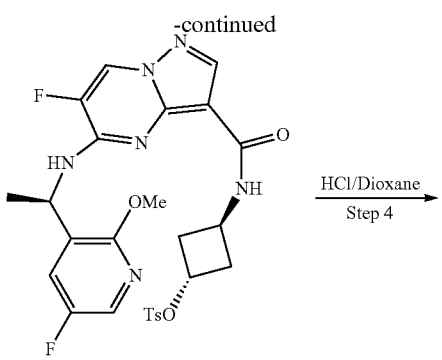

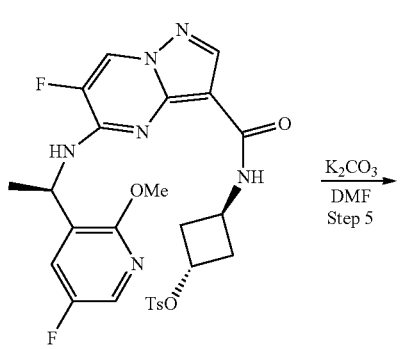

Step 1: Preparation of ethyl (R)-6-fluoro-5-((1-(5-fluoro-2-methoxypyridin-3-yl)ethyl)amino)pyrazolo[1,5-c]pyrimidine-3-carboxylate

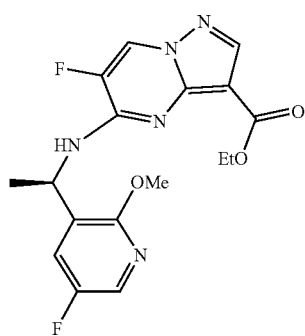 [SMILES: CCOC(=O)c1cnn2cc(F)c(N[C@H](C)c3cc(F)cnc3OC)nc12]

(R)-1-(5-fluoro-2-methoxypyridin-3-yl)ethyl-1-amine hydrochloride (1.0 g) was dissolved in acetonitrile (20 mL), and then added with N,N-Diisopropylethylamine (1.9 g) and ethyl 5-chloro-6-fluoropyrazo[1,5-c]pyrimidine-3-carboxylate (1.2 g) in sequence. The obtained mixture reacted at 60° C. for 3 hours. TLC showed that the reaction was complete. The reaction solution was poured into water (50 mL), and extracted with dichloromethane, and organic phases were combined, washed with a saturated sodium chloride solution, dried with anhydrous sodium sulfate, filtered and concentrated. The obtained crude product was purified by column chromatography to obtain 1.1 g of the title compound.

MS (ESI) m/z (M+H)$^+$=378.2.

$^1$H NMR (400 MHz, DMSO-d$_6$) δ 9.15 (d, J=6.4 Hz, 1H), 8.49 (d, J=8.0 Hz, 1H), 8.18 (s, 1H), 8.02 (d, J=3.2 Hz, 1H), 7.67 (dd, J=9.0, 3.0 Hz, 1H), 5.60-5.52 (m, 1H), 4.18-4.10 (m, 2H), 3.93 (s, 3H), 1.50 (d, J=6.8 Hz, 3H), 1.22 (t, J=7.0 Hz, 3H).

Step 2: Preparation of (R)-6-fluoro-5-(((1-(5-fluoro-2-methoxypyridin-3-yl)ethyl)amino)pyrazolo[1,5-c]pyrimidine-3-carboxylic acid

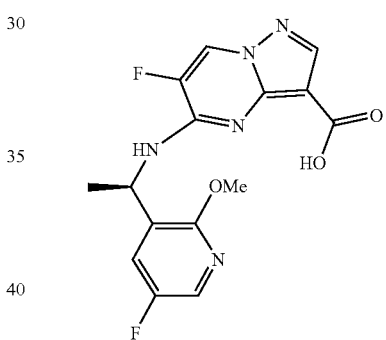

At room temperature, ethyl (R)-6-fluoro-5-((1-(5-fluoro-2-methoxypyridin-3-yl)ethyl)amino)pyrazolo[1,5-c]pyrimidine-3-carboxylate (1.1 g) was dissolved in an ethanol/water (5 mL/15 mL) mixed solution, and then added with sodium hydroxide (584 mg). The obtained mixture reacted at 50° C. overnight. TLC showed that the reaction was complete. The reaction solution was concentrated to remove ethanol, and the residual solution was poured into water (20 mL). The pH was adjusted to about 5 with a hydrogen chloride solution (2 M). The solution was extracted with dichloromethane, and organic phases were combined, washed with a saturated sodium chloride solution, dried with anhydrous sodium sulfate, filtered and concentrated to obtain 800 mg of crude product, which could be directly used in the next step without purification.

MS (ESI) m/z (M+H)$^+$=350.1.

$^1$H NMR (400 MHz, DMSO-d$_6$) δ 11.68 (s, 1H), 9.13 (d, J=6.0 Hz, 1H), 8.51 (d, J=7.6 Hz, 1H), 8.14 (s, 1H), 8.01 (d, J=2.8 Hz, 1H), 7.72 (dd, J=9.0, 3.0 Hz, 1H), 5.59-5.52 (m, 1H), 3.92 (s, 3H), 1.50 (d, J=6.8 Hz, 3H).

Step 3: Preparation of cyclobutyl ((1R,3R)-3-(6-fluoro-5-(((R)-1-(5-fluoro-2-methoxypyridin-3-yl)ethyl)amino)pyrazolo[1,5-c]pyrimidine-3-carboxamido)-4-methylbenzenesulfonate

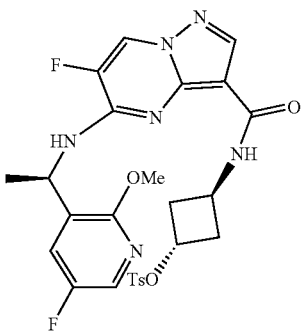 [SMILES: COc1ncc(F)cc1[C@@H](C)Nc1nc2c(C(=O)N[C@H]3C[C@H](OS(=O)(=O)c4ccc(C)cc4)C3)cnn2cc1F]

(R)-6-fluoro-5-(((1-(5-fluoro-2-methoxypyridin-3-yl)ethyl)amino)pyrazolo[1,5-c]pyrimidine-3-carboxylic acid (800 mg), 2-(7-azobenzotriazole)-N,N,N',N'-tetramethyl-urea hexafluorophosphate (1.0 g) and N,N-Diisopropylethylamine (886 mg) were dissolved in dried tetrahydrofuran (10 mL). The obtained mixture reacted at room temperature for 1 hour, and then added with tert-butyl (3-hydroxycyclobutyl)carbamate hydrochloride (953 mg) for continuous reaction for 1 hour. TLC showed that the reaction was complete. The reaction solution was poured into water (30 mL), and extracted with ethyl acetate, and organic phases were combined, washed with a saturated sodium chloride solution, dried with anhydrous sodium sulfate, filtered and concentrated. The obtained crude product was purified by column chromatography to obtain 800 mg of the title compound.

MS (ESI) m/z (M+H)$^+$=573.2.

$^1$H NMR (400 MHz, DMSO-$d_6$) δ 9.21 (d, J=6.0 Hz, 1H), 8.57 (d, J=7.6 Hz, 1H), 8.09 (s, 1H), 8.05 (d, J=2.8 Hz, 1H), 7.80-7.78 (m, 2H), 7.66 (dd, J=8.8, 2.8 Hz, 1H), 7.60 (d, J=6.8 Hz, 1H), 7.47 (d, J=8.0 Hz, 2H), 5.44-5.37 (m, 1H), 4.96-4.92 (m, 1H), 4.33-4.28 (m, 1H), 3.80 (s, 3H), 2.47-2.38 (m, 5H), 2.24-2.18 (m, 1H), 2.12-2.08 (m, 1H), 1.52 (d, J=6.8 Hz, 3H).

Step 4: Preparation of cyclobutyl ((1R,3R)-3-(6-fluoro-5-(((R)-1-(5-fluoro-2-hydroxypyridin-3-yl)ethyl)amino)pyrazolo[1,5-a]pyrimidine-3-carboxamido)-4-methylbenzenesulfonate

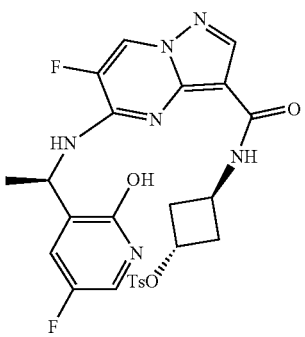

Cyclobutyl (1R,3R)-3-(6-fluoro-5-(((R)-1-(5-fluoro-2-methoxypyridin-3-yl)ethyl)amino)pyrazolo[1,5-c]pyrimidine-3-carboxamido)-4-methylbenzenesulfonate (800 mg) was dissolved 1,4-dioxane of hydrogen chloride (4 M, 10 mL). The obtained mixture reacted at 55° C. overnight. TLC showed that the reaction was complete. The reaction solution was directly concentrated to remove most of the 1,4-dioxane to obtain 600 mg of crude product, which could be directly used in the next step without purification.

MS (ESI) m/z (M+H)$^+$=559.2.

Step 5: Preparation of (3$^1$S,3$^3$S,6$^3$E,6$^4$E,8R)-1$^5$,6$^6$-difluoro-8-methyl-2-oxo-4,7-diaza-6(3,5)-pyrazolo[1,5-c]pyrimidine-1(2,3)-pyridine-3(1,3)-cyclobutyl-cyclooctane-5-one Cyclobutyl (1R,3R)-3-(6-fluoro-5-(((R)-1-(5-fluoro-2-hydroxypyridin-3-yl)ethyl)amino)pyrazolo[1,5-c]pyrimidine-3-carboxamido)-4-methylbenzenesulfonate (250 mg) was dissolved in N,N-Dimethylformamide (6 mL), and then added with potassium carbonate (232 mg). The system reacted at room temperature for 5 hours. TLC showed that the reaction was complete. The system was poured into water (10 mL), and extracted with ethyl acetate, and organic phases were combined, washed with a saturated sodium chloride solution, dried with anhydrous sodium sulfate, filtered and concentrated. The obtained crude product was purified by preparative thin-layer chromatography and purified by preparative high-performance liquid chromatography to obtain 58.0 mg of the title compound, wherein ee value was higher than 99.5%. $^1$H NMR data of the compound is shown in FIG. 1.

MS (ESI) m/z (M+H)$^+$=387.1.

$^1$H NMR (400 MHz, DMSO-$d_6$) δ 9.22-9.16 (m, 1H), 9.15 (d, J=12.0 Hz, 1H), 8.93 (d, J=8.0 Hz, 1H), 8.10 (s, 1H), 8.05 (d, J=4.0 Hz, 1H), 7.87 (dd, J=8.8, 3.0 Hz, 1H), 5.79-5.67 (m, 1H), 5.15-5.12 (m, 1H), 4.70-4.63 (m, 1H), 3.10-3.04 (m, 1H), 2.92-2.86 (m, 1H), 2.18-2.12 (m, 1H), 1.69-1.63 (m, 1H), 1.54 (d, J=8.0 Hz, 3H).

Example 4

Preparation of (3¹S,3³S,6³E,6⁴E,8R)-8-methyl-2-oxo-4,7-diaza-6(3,5)-pyrazolo[1,5-a]pyrimidine-1(2,3)-pyridine-3(1,3)-cyclobutylcyclooctane-5-one

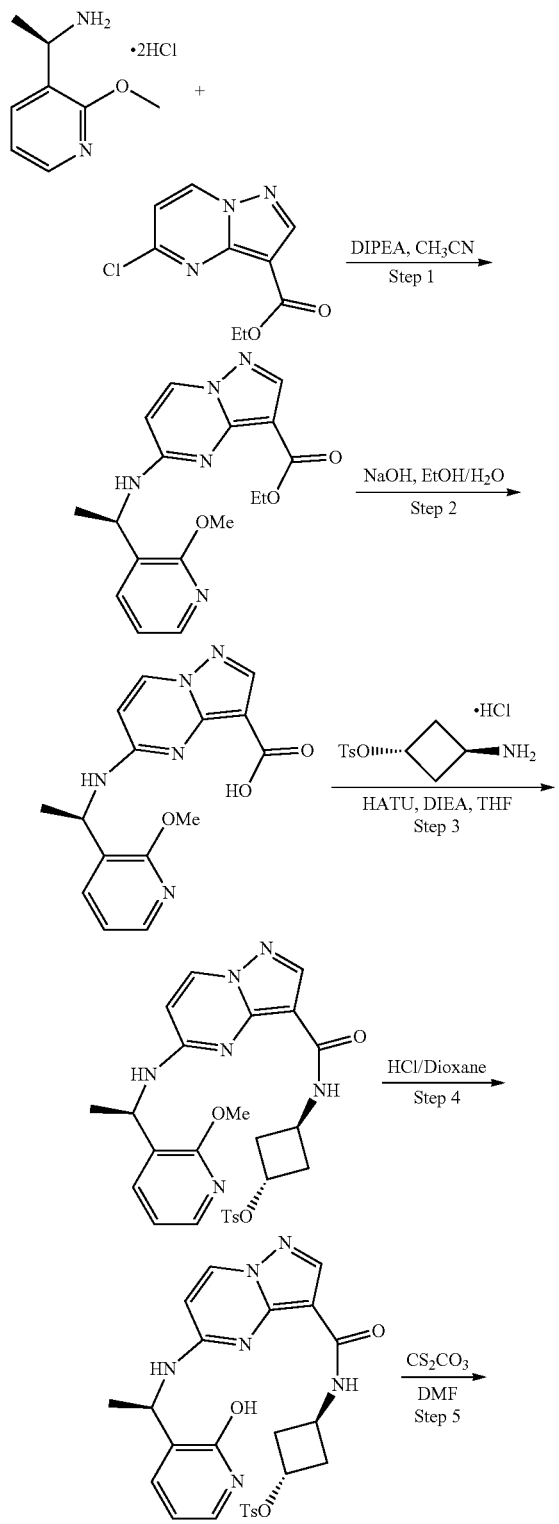

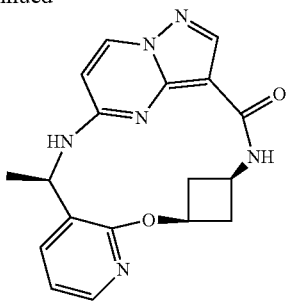

Step 1: Preparation of ethyl (R)-5-((1-(2-methoxypyridin-3-yl)ethyl)amino)pyrazolo[1,5-c]pyrimidine-3-carboxylate

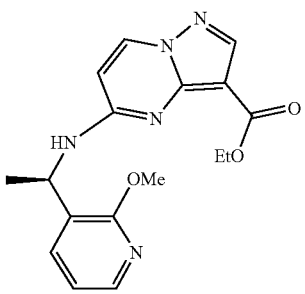

(R)-1-(2-methoxypyridin-3-yl)ethyl-1-amine hydrochloride (360 mg) was dissolved in acetonitrile (20 mL), and then added with N,N-Diisopropylethylamine (831 mg) and ethyl 5-chlorofluoropyrazo[1,5-c]pyrimidine-3-carboxylate (398 mg) in sequence. The obtained mixture reacted at 60° C. for 3 hours. TLC showed that raw materials were completely consumed. The reaction solution was poured into 50 mL of water, and extracted with dichloromethane, and organic phases were washed with a saturated sodium chloride solution, dried with anhydrous sodium sulfate, filtered and concentrated. The obtained crude product was purified by column chromatography to obtain 240 mg of the title compound.

MS (ESI) m/z (M+H)⁺=342.2

Step 2: Preparation of (R)-5-((1-(2-methoxypyridin-3-yl)ethyl)amino)pyrazolo[1,5-c]pyrimidine-3-carboxylic acid

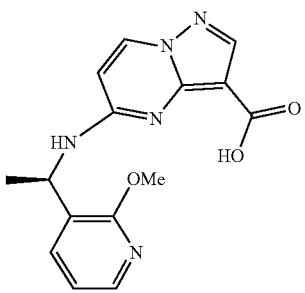 [SMILES: CCOC(=O)c1cnn2ccc(N[C@H](C)c3cccnc3OC)nc12]

Ethyl (R)-5-((1-(2-methoxypyridin-3-yl)ethyl)amino)pyrazolo[1,5-a]pyrimidine-3-carboxylate (240 mg) was dissolved in an ethanol/water (3 mL/9 mL) mixed solution, and then added with sodium hydroxide (140 mg) at room temperature. The obtained mixture reacted at 50° C. overnight. After the reaction was complete, the reaction solution was concentrated to remove ethanol, and then poured into water (20 mL). The pH was adjusted to about 5 with an aqueous hydrochloric acid solution (2 N). The solution was extracted with dichloromethane, and organic phases were washed with a saturated sodium chloride solution, dried with anhydrous sodium sulfate, filtered and concentrated to obtain 191 mg of the title compound, which could be directly used in the next step without purification.

MS (ESI) m/z (M+H)$^+$=314.1

Step 3: Preparation of cyclobutyl (1R,3R)-3-(5-(((R)-1-(2-methoxypyridin-3-yl)ethyl)amino)pyrazolo[1,5-a]pyrimidine-3-carboxamido)4-methylbenzenesulfonate

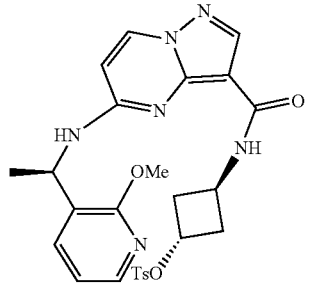 [SMILES: COc1ncccc1[C@@H](C)Nc1ccn2ncc(C(=O)N[C@H]3C[C@H](OS(=O)(=O)c4ccc(C)cc4)C3)c2n1]

(R)-5-((1-(2-methoxypyridin-3-yl)ethyl)amino)pyrazolo[1,5-c]pyrimidine-3-carboxylic acid (191 mg), O-(7-azabenzotriazole-1-yl)-N,N,N'N'-tetramethylurea hexafluorophosphate (255 mg) and N,N-Diisopropylethylamine (197 mg) were dissolved in dried tetrahydrofuran (10 mL). The obtained mixture reacted at room temperature for 1 hour, and then added with (1R,3R)-3-(4-methylphenylsulfonyloxy)cyclobutanamine hydrochloride (219 mg) for continuous reaction for 1 hour. The reaction solution was poured into 30 mL of water, and extracted with ethyl acetate for three times, and organic phases were washed with a saturated sodium chloride solution, combined, dried with anhydrous sodium sulfate, filtered and concentrated. The obtained crude product was purified by column chromatography to obtain 270 mg of the title compound.

MS (ESI) m/z (M+H)$^+$=537.2

Step 4: Preparation of cyclobutyl (1R,3R)-3-(5-(((R)-1-(2-hydroxypyridin-3-yl)ethyl)amino)pyrazolo[1,5-a]pyrimidine-3-carboxamido)4-methylbenzenesulfonate

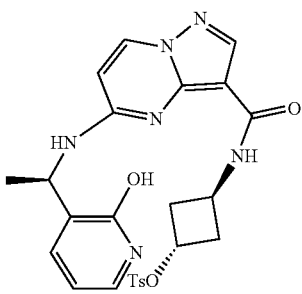 [SMILES: Cc1ccc(S(=O)(=O)O[C@H]2C[C@H](NC(=O)c3cnn4ccc(N[C@H](C)c5cccnc5O)nc34)C2)cc1]

Cyclobutyl (1R,3r)-3-(5-(((R)-1-(2-methoxypyridin-3-yl)ethyl)amino)pyrazolo[1,5-a]pyrimidine-3-carboxamido)4-methylbenzenesulfonate (270 mg) was dissolved 1,4-dioxane of hydrogen chloride (4 M, 10 mL). The obtained mixture reacted at 55° C. overnight. After the reaction was complete, the reaction solution was concentrated to remove most of the 1,4-dioxane to obtain 250 mg of the title compound, which could be directly used for next reaction without purification.

MS (ESI) m/z (M+H)$^+$=523.2

Step 5: Preparation of $(3^1S,3^3S,6^3E,6^4E,8R)$-8-methyl-2-oxo-4,7-diaza-6(3,5)-pyrazolo[1,5-a]pyrimidine-1(2,3)-pyridine-3(1,3)-cyclobutylcyclooctane-5-one Cyclobutyl (1R,3R)-3-(5-(((R)-1-(2-hydroxypyridin-3-yl)ethyl)amino)pyrazolo[1,5-a]pyrimidine-3-carboxamido)4-methylbenzenesulfonate (130 mg) was dissolved in N,N-Dimethylformamide (6 mL), and then added with cesium carbonate (299 mg). After the addition was complete, the obtained mixture reacted at room temperature for 5 hours. TLC showed that the reaction was complete. The reaction solution was poured into 10 mL of water, and extracted with ethyl acetate for three times, and organic phases were combined, washed with a saturated sodium chloride solution, dried with anhydrous sodium sulfate, filtered and concentrated. The obtained crude product was purified by preparative HPLC to obtain 36.6 mg of the title compound.

MS (ESI) m/z (M+H)$^+$=351.2

$^1$H NMR (400 MHz, d$_6$-DMSO) δ 9.29 (1H, d, J=10.8 Hz), 8.84 (1H, d, J=7.2 Hz), 8.56 (1H, d, J=7.6 Hz), 8.04-8.02 (2H, m), 7.75 (1H, dd, J=7.6 Hz, 2.0 Hz), 7.03-

7.00 (1H, m), 6.37 (1H, d, J=7.6 Hz), 5.69-5.62 (1H, m), 5.15-5.12 (1H, m), 4.69-4.62 (1H, m), 3.08-3.02 (1H, m), 2.91-2.85 (1H, m), 2.16-2.11 (1H, m), 1.70-1.65 (1H, m), 1.45 (3H, d, J=7.2 Hz).

Example 5

Preparation of (3¹S,3³S,6³E,6⁴E,8R)-6⁶-fluoro-8-methyl-2-oxo-4,7-diaza-6(3,5)-pyrazolo[1,5-a]pyrimidine-1(2,3)-pyridine-3(1,3)-cyclobutylcyclooctane-5-one

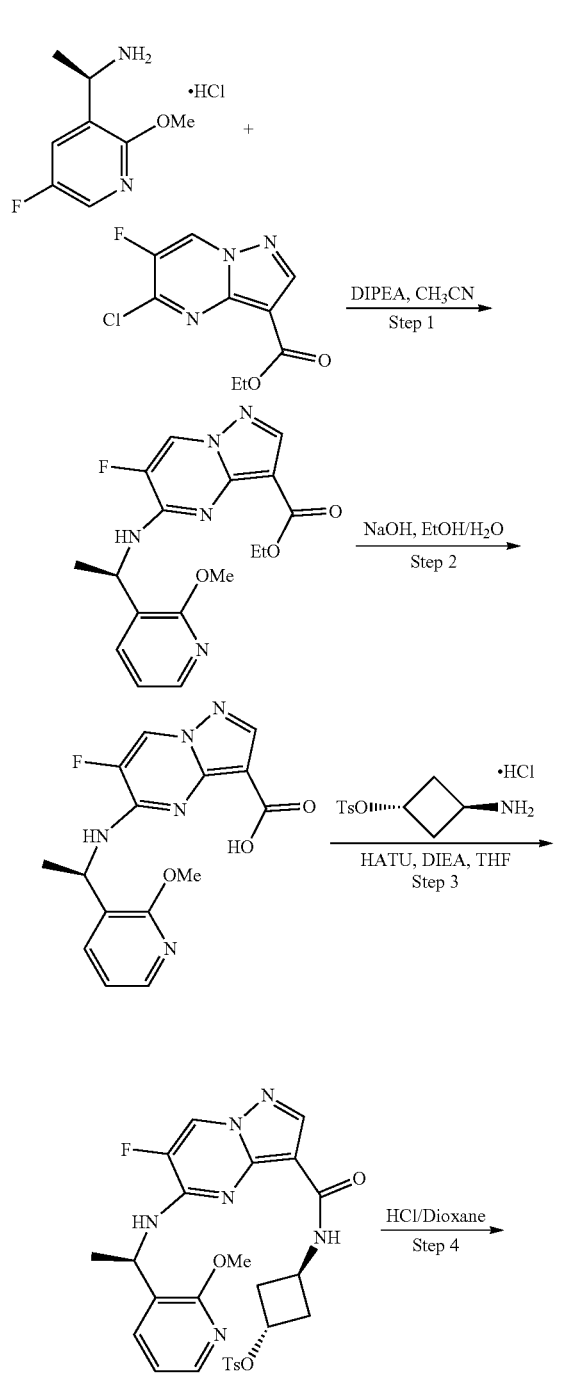

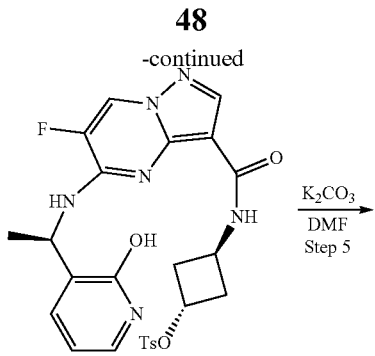

Step 1: Preparation of ethyl (R)-6-fluoro-5-((1-(2-methoxypyridin-3-yl)ethyl)amino)pyrazolo[1,5-c]pyrimidine-3-carboxylate (R)-1-(2-methoxypyridin-3-yl)ethyl-1-amine hydrochloride (390 mg) was dissolved in acetonitrile (20 mL), and then added with N,N-Diisopropylethylamine (898 mg) and ethyl 5-chloro-6-flupyrazolo[1,5-c]pyrimidine-3-carboxylate (508 mg) in sequence. The obtained mixture reacted at 60° C. for 3 hours. TLC showed that raw materials were completely consumed. The reaction solution was poured into 50 mL of water, and extracted with dichloromethane for three times, and organic phases were combined, washed with a saturated sodium chloride solution, dried with anhydrous sodium sulfate, filtered and concentrated. The obtained crude product was purified by column chromatography to obtain 420 mg of the title compound.

MS (ESI) m/z (M+H)⁺=360.2

Step 2: Preparation of (R)-6-fluoro-5-((1-(2-methoxypyridin-3-yl)ethyl)amino)pyrazolo[1,5-a]pyrimidine-3-carboxylic acid

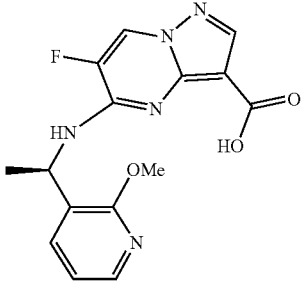 [SMILES: COc1ncccc1[C@@H](C)Nc1nc2c(C(=O)O)cnn2cc1F]

Ethyl (R)-6-fluoro-5-((1-(2-methoxypyridin-3-yl)ethyl)amino)pyrazolo[1,5-a]pyrimidine-3-carboxylate (420 mg) was dissolved in an ethanol/water (4 mL/12 mL) mixed solution, and then added with sodium hydroxide (187 mg) at room temperature. After the addition was complete, the obtained mixture reacted at 50° C. overnight. After the reaction was complete, the reaction solution was concentrated to remove ethanol, and then poured into water (20 mL). The pH was adjusted to about 5 with an aqueous hydrochloric acid solution (2 N). The solution was extracted with dichloromethane for three times, and organic phases were combined, washed with a saturated sodium chloride solution, dried with anhydrous sodium sulfate, filtered and concentrated to obtain 356 mg of the title compound, which could be directly used in the next step without purification.
MS (ESI) m/z (M+H)$^+$=332.1

Step 3: Preparation of cyclobutyl (1R,3R)-3-(6-fluoro-5-(((R)-1-(2-methoxypyridin-3-yl)ethyl)amino)pyrazolo[1,5-a]pyrimidine-3-carboxamido)4-methylbenzenesulfonate

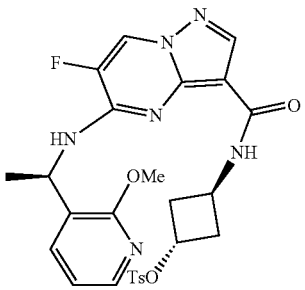 [SMILES: COc1ncccc1[C@@H](C)Nc1nc2c(C(=O)N[C@H]3C[C@H](OS(=O)(=O)c4ccc(C)cc4)C3)cnn2cc1F]

(R)-6-fluoro-5-((1-(2-methoxypyridin-3-yl)ethyl)amino)pyrazolo[1,5-a]pyrimidine-3-carboxylic acid (356 mg), O-(7-azabenzotriazole-1-yl)-N,N,N',N'-tetramethylurea hexafluorophosphate (494 mg) and N,N-Diisopropylethylamine (418 mg) were dissolved in dried tetrahydrofuran (10 mL). The obtained mixture reacted at room temperature for 1 hour, and then added with (1R,3R)-3-(4-methylphenylsulfonyloxy)cyclobutanamine hydrochloride (388 mg) for continuous reaction for 1 hour. The reaction solution was poured into 30 mL of water, and extracted with ethyl acetate for three times, and organic phases were combined, washed with a saturated sodium chloride solution, dried with anhydrous sodium sulfate, filtered and concentrated. The obtained crude product was purified by column chromatography to obtain 500 mg of the title compound.
MS (ESI) m/z (M+H)$^+$=555.2

Step 4: Preparation of cyclobutyl (1R,3R)-3-(6-fluoro-5-(((R)-1-(2-hydroxypyridin-3-yl)ethyl)amino)pyrazolo[1,5-c]pyrimidine-3-carboxamido)4-methylbenzenesulfonate

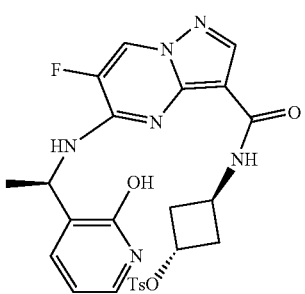 [SMILES: Cc1ccc(S(=O)(=O)O[C@H]2C[C@H](NC(=O)c3cnn4cc(F)c(N[C@H](C)c5cccnc5O)nc34)C2)cc1]

Cyclobutyl (1R,3R)-3-(6-fluoro-5-(((R)-1-(2-methoxypyridin-3-yl)ethyl)amino)pyrazolo[1,5-c]pyrimidine-3-carboxamido)4-methylbenzenesulfonate (500 mg) were added into 1,4-dioxane of hydrogen chloride (4 M, 10 mL). The obtained mixture reacted at 55° C. overnight. After the reaction was complete, the reaction solution was concentrated to remove most of the 1,4-dioxane to obtain 280 mg of the title compound, which could be directly used for next reaction without purification.
MS (ESI) m/z (M+H)$^+$=541.2

Step 5: Preparation of (3$^1$S,3$^3$S, 6$^3$E,6$^4$E,8R)-6$^6$-fluoro-8-methyl-2-oxo-4,7-diaza-6(3,5)-pyrazolo[1,5-c]pyrimidine-1(2,3)-pyridine-3(1,3)-cyclobutylcyclooctane-5-one

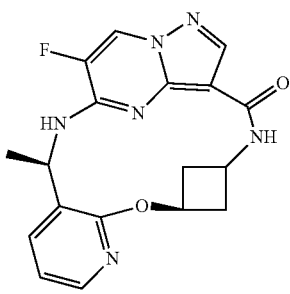

Cyclobutyl (1R,3R)-3-(6-fluoro-5-(((R)-1-(2-hydroxypyridin-3-yl)ethyl)amino)pyrazolo[1,5-c]pyrimidine-3-carboxamido)4-methylbenzenesulfonate (150 mg) was dissolved in N,N-Dimethylformamide (6 mL), and then added with potassium carbonate (144 mg). After the addition was complete, the obtained mixture reacted at room temperature for 5 hours. The reaction solution was poured into 10 mL of water, and extracted with ethyl acetate for three times, and organic phases were combined, washed with a saturated sodium chloride solution, dried with anhydrous sodium sulfate, filtered and concentrated. The obtained crude product was purified by preparative HPLC to obtain 45.2 mg of the title compound.

MS (ESI) m/z (M+H)$^+$=369.2

$^1$H NMR (400 MHz, d$_6$-DMSO) δ 9.21-9.15 (2H, m), 9.02 (1H, d, J=7.6 Hz), 8.08 (1H, s), 8.04-8.02 (1H, m), 7.92 (1H, dd, J=7.6 Hz, 5.2 Hz), 7.05-7.02 (1H, m), 5.80-5.73 (1H, m), 5.17-5.13 (1H, m), 4.70-4.63 (1H, m), 3.09-3.03 (1H, m), 2.92-2.86 (1H, m), 2.17-2.12 (1H, m), 1.70-1.64 (1H, m), 1.52 (3H, d, J=7.2 Hz).

Example 6

Preparation of (3$^1$S,3$^3$S,6$^3$Z,6$^4$E,8R)-1$^5$,6$^2$-difluoro-8-methyl-2-oxo-4,7-diaza-6(3,5)-pyrazolo[1,5-a]pyrimidine-1(2,3)-pyridine-3(1,3)-cyclobutylcyclooctane-5-one

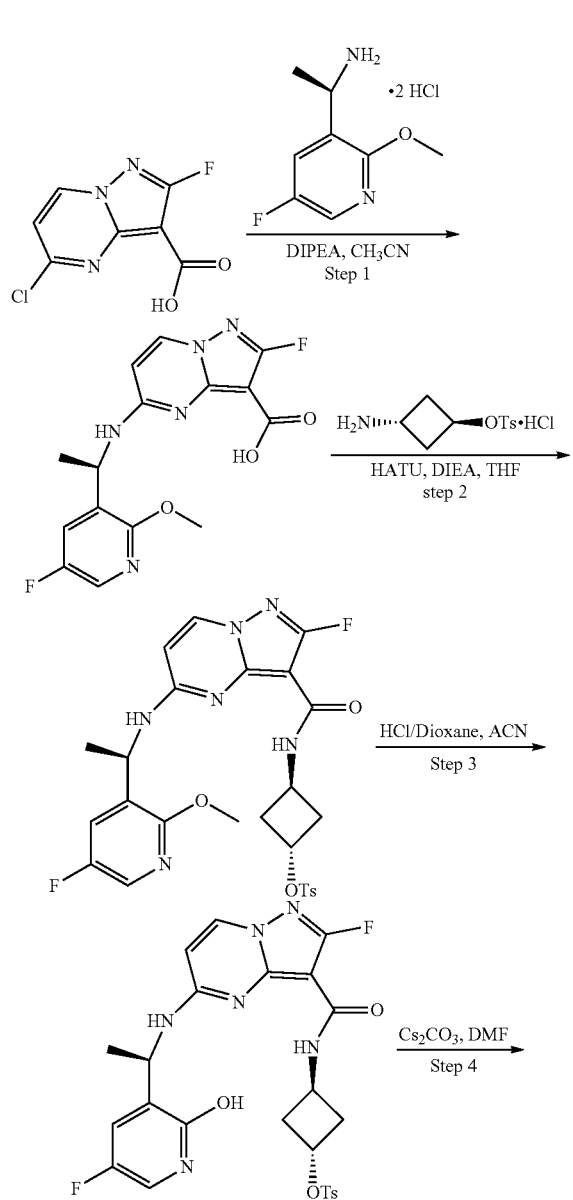

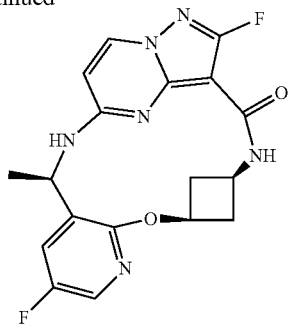

Step 1: Preparation of (R)-2-fluoro-5-((1-(5-fluoro-2-methoxypyridin-3-yl)ethyl)amino)pyrazolo[1,5-c]pyrimidine-3-carboxylic acid

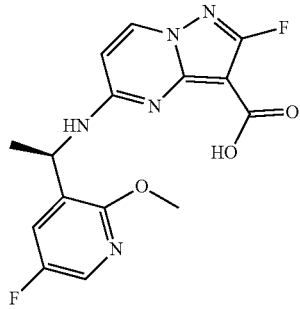 [SMILES: COc1ncc(F)cc1[C@@H](C)Nc1ccn2nc(F)c(C(=O)O)c2n1]

(R)-1-(5-fluoro-2-methoxypyridin-3-yl)ethyl-1-amine hydrochloride (702 mg) was dissolved in acetonitrile (20 mL), and then added with N,N-Diisopropylethylamine (1.2 g) and 5-chloro-2-flupyrazolo[1,5-c]pyrimidine-3-carboxylic acid (521 mg) in sequence. The obtained mixture reacted at 50° C. for 3 hours. TLC showed that raw materials were completely consumed. The reaction solution was poured into 50 mL of water, and extracted with ethyl acetate for three times, and organic phases were combined, washed with a saturated sodium chloride solution, dried with anhydrous sodium sulfate, filtered and concentrated to obtain 150 mg of crude product of the title compound.

MS (ESI) m/z (M+H)$^+$=350.2

Step 2: Preparation of cyclobutyl (1R,3R)-3-(2-fluoro-5-(((R)-1-(5-fluoro-2-methoxypyridin-3-yl)ethyl)amino)pyrazolo[1,5-a]pyrimidine-3-carboxamido)4-methylbenzenesulfonate

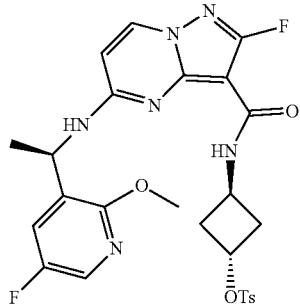 [SMILES: COc1ncc(F)cc1[C@@H](C)Nc1ccn2nc(F)c(C(=O)N[C@H]3C[C@H](OS(=O)(=O)c4ccc(C)cc4)C3)c2n1]

(R)-2-fluoro-5-((1-(5-fluoro-2-methoxypyridin-3-yl) ethyl)amino)pyrazolo[1,5-c]pyrimidine-3-carboxylic acid (150 mg, crude product), O-(7-azabenzotriazole-1-yl)-N,N,N',N'-tetramethylurea hexafluorophosphate (70 mg) and N,N-Diisopropylethylamine (222 mg) were dissolved in dried tetrahydrofuran (10 mL). The obtained mixture reacted at room temperature for 1 hour, and then added with (1R,3R)-3-(4-methylphenylsulfonyloxy)cyclobutanamine hydrochloride (119 mg) for continuous reaction for 1 hour. The reaction solution was poured into 30 mL of water, and extracted with ethyl acetate for three times, and organic phases were combined, washed with a saturated sodium chloride solution, dried with anhydrous sodium sulfate, filtered and concentrated. The obtained crude product was purified by column chromatography to obtain 240 mg of the title compound.

MS (ESI) m/z (M+H)$^+$=573.2

Step 3: Preparation of cyclobutyl (1R,3R)-3-(2-fluoro-5-(((R)-1-(5-fluoro-2-hydroxypyridin-3-yl) ethyl)amino)pyrazolo[1,5-a]pyrimidine-3-carboxamido)4-methylbenzenesulfonate

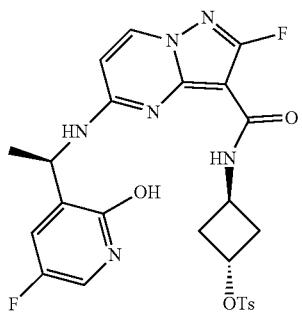 [SMILES: Cc1ccc(S(=O)(=O)O[C@H]2C[C@H](NC(=O)c3c(F)nn4ccc(N[C@H](C)c5cc(F)cnc5O)nc34)C2)cc1]

Cyclobutyl (1R,3R)-3-(2-fluoro-5-(((R)-1-(5-2-methoxypyridin-3-yl)ethyl)amino)pyrazolo[1,5-c]pyrimidine-3-carboxamido)4-methylbenzenesulfonate (240 mg) was dissolved in acetonitrile (10 mL), and then added with 1,4-dioxane of hydrogen chloride (4 M, 5 mL). The obtained mixture reacted at 60° C. overnight. After the reaction was complete, the reaction solution was concentrated to remove dioxane to obtain 154 mg of the title compound, which could be directly used for next reaction without purification.

MS (ESI) m/z (M+H)$^+$=559.2

Step 4: Preparation of (3$^1$S,3$^3$S,6$^3$Z,6$^4$E,8R)-1$^5$,6$^2$-difluoro-8-m ethyl-2-oxo-4,7-diaza-6(3,5)-pyrazolo[1,5-a]pyrimidine-1(2,3)-pyridine-3(1,3)-cyclobutyl-cyclooctane-5-one

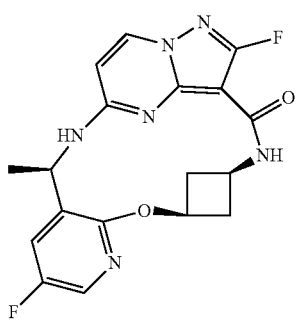 [SMILES: C[C@H]1Nc2ccn3nc(F)c(c3n2)C(=O)N[C@H]2C[C@H](C2)Oc2ncc(F)cc21]

Cyclobutyl (1R,3r)-3-(2-fluoro-5-(((R)-1-(5-fluoro-2-hydroxypyridin-3-yl)ethyl)amino)pyrazolo[1,5-c]pyrimidine-3-carboxamido)4-methylbenzenesulfonate (154 mg) was dissolved in N,N-Dimethylformamide (6 mL), and then added with cesium carbonate (144 mg). After the addition was complete, the obtained mixture reacted at room temperature for 3 hours. The reaction solution was poured into 10 mL of water, and extracted with ethyl acetate for three times, and organic phases were combined, washed with a saturated sodium chloride solution, dried with anhydrous sodium sulfate, filtered and concentrated. The obtained crude product was purified by preparative HPLC to obtain 28.0 mg of the title compound.

MS (ESI) m/z (M+H)$^+$=387.1

$^1$H NMR (400 MHz, d$_6$-DMSO) δ 9.11 (1H, d, J=10.8 Hz), 8.90 (1H, d, J=7.2 Hz), 8.46 (1H, d, J=7.6 Hz), 8.05 (1H, d, J=2.8 Hz), 7.68 (1H, dd, J=8.8 Hz, 3.2 Hz), 6.43 (1H, d, J=7.6 Hz), 5.62-5.59 (1H, m), 5.14-5.10 (1H, m), 4.66-4.64 (1H, m), 3.08-3.03 (1H, m), 2.90-2.85 (1H, m), 2.16-2.11 (1H, m), 1.69-1.64 (1H, m), 1.47 (3H, d, J=6.8 Hz).

Testing Example 1

Kinase Inhibitory Activity

Sundia Meditech (Shanghai) Co., Ltd. was commissioned to complete the testing example.

1. Experimental Purpose

Inhibitory activities of the compound of the present application on three kinases TRKa, TRKA(G595R) and TRKC(G623R) were measured.

2. Experimental Materials 2.2.1 Reagents and Consumables

| Name of reagent | Supplier | Article number | Batch number |
| --- | --- | --- | --- |
| TRKa | Carna | 08-186 | 13CBS-0565G |
| TRKA (G595R) | signalchem | N16-12BG-100 | H2714-7 |
| TRKC(G623R) | signalchem | N18-12CH-100 | D2567-8 |
| Kinase substrate 22 | GL | 112393 | P190329-SL112393 |
| DMSO | Sigma | D8418-1L | SHBG3288V |
| 384-well plate (white) | PerkinElmer | 6007290 | 810712 |

2.2.2 Instruments

Centrifuge (manufacturer: Eppendorf, model number: 5430); microplate reader (manufacturer: Perkin Elmer, model number: Caliper EZ ReaderII); and Echo 550 (manufacturer: Labcyte, model number: Echo 550)

3. Experimental Method 3.1 A tested compound was accurately weighed and dissolved in 100% DMSO to prepare into a 10 mM solution.

3.2 Kinase Reaction Process 3.2.1 1×kinase buffer was prepared.

3.2.2 Preparation of compounds of gradient concentrations: the tested compound had an initial concentration of 1000 nM, and was diluted into a 100% DMSO solution of 100 times final concentration in the 384-well plate, and then the 100% DMSO solution was diluted by 3 times to obtain DMSO solutions of the compound with 10 concentrations. 250 nL of the compound of 100 times final concentration was transferred to a reaction plate OptiPlate-384F by a dispenser Echo 550.

3.2.3 A kinase solution of 2.5 times final concentration was prepared with 1×kinase buffer.

3.2.4 10 μL of kinase solution of 2.5 times final concentration was added into a compound well and a positive control well respectively; and 10 μL of 1×kinase buffer was added into a negative control well.

3.2.5 The reaction plate was shaken and mixed evenly, and then incubated at room temperature for 10 minutes.

3.2.6 Mixed solutions of ATP and kinase substrate 22 of 5 times and 3 times final concentrations were prepared with 1×kinase buffer.

3.2.7 15 μL of mixed solution of ATP and substrate of 5 times or 3 times final concentration was added.

3.2.8 The 384-well plate was centrifuged at 1,000 rpm for 30 seconds, shaken and mixed evenly, and then incubated at room temperature for corresponding time.

3.2.9 The kinase reaction was terminated.

3.2.10 A conversion rate was read by the microplate reader Caliper EZ Reader.

4. Data Analysis

Calculation Formula

Inhibition rate %=(conversion rate % maximum−conversion rate % sample)/(conversion rate % maximum−conversion rate % minimum)×100 wherein the conversion rate % sample was: a reading number of a conversion rate of a sample; the conversion rate % minimum was: an average value of the negative control well, which represented a reading number of a conversion rate without an enzyme activity well; and the conversion rate % maximum was: an average value of a ratio of the positive control well, which represented a reading number of a conversion rate without a compound inhibition well.

Fitting of dose-effect curve: a log value of concentration was used as an X axis, a percentage inhibition rate was used as a Y axis, and the dose-effect curve was fitted by a log (inhibitor) vs. response-variable slope of the analysis software GraphPad Prism 5 (four-parameter model fitting), so as to obtain an $IC_{50}$ value of each compound on enzyme activity.

Results are shown in the following Table 1:

TABLE 1

| IC$_{50}$ values of inhibitory activities of the compound of the present application on three kinases | | | |
|---|---|---|---|
| Serial number of example | TRKa IC$_{50}$ (nM) | TRKA(G595R) IC$_{50}$ (nM) | TRKC(G623R) IC$_{50}$ (nM) |
| 1 | 0.62 | 2.50 | 3.70 |
| LOXO-195 | 0.47 | 1.60 | 2.50 |
| 2 | 0.42 | 1.20 | 1.80 |
| Positive control 1 | 0.39 | 0.72 | 1.70 |
| 3 | 0.36 | 0.89 | 1.50 |
| Positive control 2 | 0.43 | 0.97 | 1.40 |
| 4 | 320 | >1000 | >1000 |
| 5 | 127 | 561 | >1000 |
| 6 | 0.52 | 2.90 | 8.20 |

LOXO-195 is a second generation TRK inhibitor, with the following chemical structure:

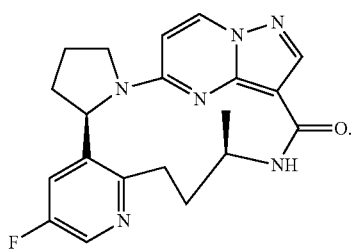 [SMILES: C[C@@H]1CCc2ncc(F)cc2[C@H]2CCCN2c2ccn3ncc(c3n2)C(=O)N1]

The positive control 1 is the compound in example 5 of patent WO2019210835, with the following chemical structure:

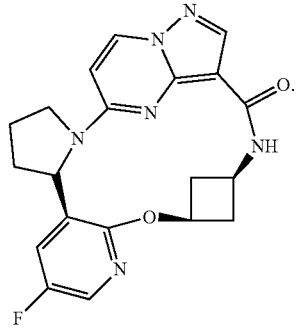

The positive control 2 is the compound in example 6 of patent WO2019210835, with the following chemical structure:

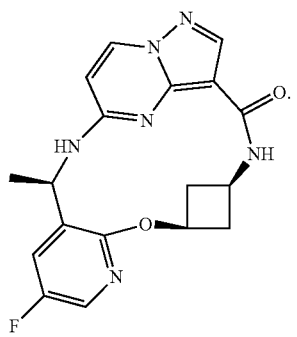 [SMILES: C[C@H]1Nc2ccn3ncc(c3n2)C(=O)N[C@H]2C[C@H](C2)Oc2ncc(F)cc21]

From biological activity data of the compound in the specific examples, the compound of the present application has high inhibitory activities on three kinases TRKa, TRKA (G595R) and TRKC(G623R). Examples 3 to 6 show that effects of fluorine substitution at different positions on the inhibitory activities on three kinases are quite different, and the fluorine substitution at different positions produces unexpected technical effects.

Testing Example 2

In-Vitro Cell Viability

Hefei Precedo Biomedical Technology Co., Ltd. was commissioned to complete the testing example, and NTRK mutant cells used were constructed by this company.

1. Experimental Purpose

Inhibitory effects of the compound of the present application on growth of three NTRK mutant cells (Ba/F3 LMNA-NTRK1-G667C, Ba/F3 EVT6-NTRK3-G623R and Ba/F3 LMNA-NTRK1-G595R) were measured.

2. Reagents and Consumables

Cell Lines:

| Cell line | Cell type | Quantity of cells/well | Medium |
|---|---|---|---|
| Ba/F3 LMNA-NTRK1-G667C | Suspension | 3000 | RPMI-1640 + 10% FBS |
| Ba/F3 EVT6-NTRK3-G623R | Suspension | 3000 | RPMI-1640 + 10% FBS |
| Ba/F3 LMNA-NTRK1-G595R | Suspension | 3000 | RPMI-1640 + 10% FBS |

Reagents:

Fetal calf serum FBS (GBICO, Cat #10099-141); CellTiter-Glo® Luminescent Cell Viability Assay (CTG, Promega, Cat #G7573); 96-well transparent flat-bottom black wall panel (Thermo®, Cat #165305); and RPMI-1640 (Hyclone, Cat #SH30809.01).

3. Experimental Process

3.1 Cell Culture and Inoculation:

Cells in logarithmic growth phase were collected and counted by a blood platelet counter, a cell concentration was adjusted to 3 to $6 \times 10^4$ cell/mL, 90 μL of cell suspension was added into a 96-well plate, and cells in the 96-well plate were cultured at 37° C. under 5% $CO_2$ and 95% humidity overnight.

3.2 Drug Dilution and Addition:

The to-be-tested compound was prepared into a 10 times drug solution in a medium containing 1% DMSO, with a highest concentration of 10 and the drug solution was diluted by 3 times in sequence to obtain drug solutions with 9 concentrations in total. More than 10 μL of prepared drug solution was added into each well of the 96-well plate in which the cells were inoculated. Then, 90 μL of medium containing 1% DMSO was added to obtain a drug solution with a highest concentration of 1 μM, and the drug solution was diluted by 3 times in sequence to obtain drug solutions with 9 concentrations in total. A final concentration of DMSO in each well was 0.1%, and three multiple wells were provided for the drug of each concentration. The cells in the 96-well plate in which the drug has been added were cultured at 37° C. under 5% $CO_2$ and 95% humidity for 72 hours, and then subjected to CTG analysis.

3.3 End-Point Plate Reading

An equal volume of CTG solution was added into each well, the 96-well plate was placed at room temperature for 20 minutes to stabilize a luminescence signal, and a luminescence value was read.

4. Data Processing

Data was analyzed by GraphPad Prism 7.0 software, and fitted by nonlinear S-curve regression to obtain a dose-effect curve, from which an $IC_{50}$ value was calculated.

Cell survival rate (%)=(Lum to-be-tested drug−Lum medium control)/(Lum cell control−Lum medium control)×100%.

Experimental results are shown in the following Table 2:

TABLE 2

$IC_{50}$ values of inhibitory activities of the compound of the present application on three cells

| Number of example | Ba/F3 LMNA-NTRK1-G595R $IC_{50}$ (nM) | Ba/F3 EVT6-NTRK3-G623R $IC_{50}$ (nM) | Ba/F3 LMNA-NTRK1-G667C $IC_{50}$ (nM) |
|---|---|---|---|
| 1 | 13 | 190 | 5.9 |
| LOXO-195 | 12 | 145 | 6.3 |
| 2 | 2.3 | 14 | 3.0 |
| Positive control 1 | 1.8 | 18 | 1.8 |
| 3 | 4.5 | 25 | 3.2 |
| Positive control 2 | 13 | 107 | 6.5 |
| 4 | >1000 | >1000 | >1000 |
| 5 | >1000 | >1000 | >1000 |
| 6 | 116 | 536 | 40 |

LOXO-195 is a second generation TRK inhibitor, with the following chemical structure:

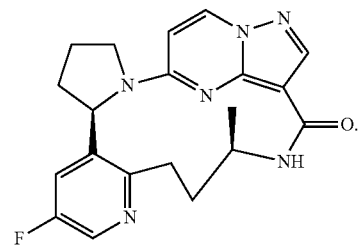 [SMILES: C[C@@H]1CCc2ncc(F)cc2[C@H]2CCCN2c2ccn3ncc(c3n2)C(=O)N1]

The positive control 1 is the compound in example 5 of patent WO2019210835, with the following chemical structure:

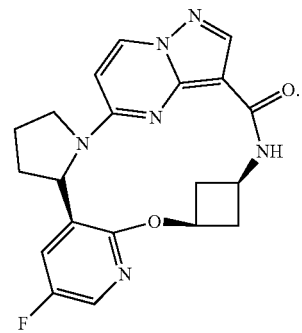

The positive control 2 is the compound in example 6 of patent WO2019210835, with the following chemical structure:

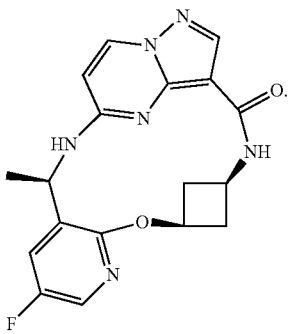 [SMILES: C[C@H]1Nc2ccn3ncc(c3n2)C(=O)N[C@H]2C[C@H](C2)Oc2ncc(F)cc21]

From biological activity data of the compound in the specific examples, the compound of the present application has strong growth inhibition effects on three NTRK mutant cells (Ba/F3 LMNA-NTRK1-G667C, Ba/F3 EVT6-NTRK3-G623R and Ba/F3 LMNA-NTRK1-G595R). The inhibitory activities of the compounds in example 1 and example 2 on three NTRK mutant cells are not significantly different from those of the corresponding positive compound, but the inhibitory activities of the compound in example 3 of the present application on three NTRK mutant cells are significantly higher than those of the corresponding positive control 2. Examples 3 to 6 show that effects of fluorine substitution at different positions on the inhibitory activities on three NTRK mutant cells are quite different, and the fluorine substitution at different positions produces unexpected technical effects.

From the point of view of clinical medication, according to data of Ba/F3 EVT6-NTRK3-G623R in Table 2, the inhibitory activity of the compound in example 3 of the present application is 4 times higher than that of the positive control compound 2, and only a lower dosage is needed clinically for a patient with NTRK3-G623R mutation.

Testing Example 3

Stability Test in Liver Microsomes

1. Experimental Purpose

A stability of the compound of the present application in liver microsomes of human, rat and mouse was measured.

2. Experimental Materials and Instruments
Reagents and Consumables:

| Name of reagent | Supplier | Item number | Batch number |
|---|---|---|---|
| Liver microsome of human | BiolVT | X008070 | SDL |
| Liver microsome of rat | BiolVT | M00001 | TIQ |
| Liver microsome of mouse | Biopredic | MIC255037 | BQM |

3. Experimental Steps 3.1 A buffer and a liver microsome were prepared into an incubation solution according to the following table:

| Reagent | Concentration | Volume |
|---|---|---|
| Phosphate buffer | 100 mM | 216.25 μL |
| Liver microsome | 20 mg/mL | 6.25 μL |

3.2 The following two experiments were carried out respectively: a) incubation system added with coenzyme factor NADPH: 25 μL of NADPH (10 mM) was added into an incubation solution (mainly comprising a liver microsome and a phosphate buffer), so that final concentrations of the liver microsome and the NADPH were 0.5 mg/mL and 1 mm respectively; and b) incubation system without coenzyme factor NADPH: 25 μL of phosphate buffer (100 mM) was added into the incubation solution, so that the final concentration of the liver microsome was 0.5 mg/mL. The incubation systems above were preheated at 37° C. for 10 minutes respectively.

3.3 2.5 μL of positive control compound or a tested compound solution (100 μM) was added into the incubation systems described in "step 3.2" above respectively for reaction, and the positive control compound was verapamil (purchased from Sigma), so that a final concentration of the tested compound of the present application or the positive control compound was 1 μM. The incubation solution added with the compound was incubated in water at 37° C. in batches.

3.4 30 μL of aliquot was taken from a reaction solution after 0.5 minute, 5 minutes, 15 minutes, 30 minutes and 45 minutes respectively, and the reaction was terminated by adding 5 times volume of cold acetonitrile containing 200 nM caffeine and 100 nM tolbutamide. The aliquot was centrifuged at a gravity acceleration of 3,220 g for 40 minutes, and 100 μL of supernatant was mixed with 100 μL of ultrapure water, and then used for LC-MS/MS analysis.

3.5 Data Analysis

A peak area was determined by an extracted ion chromatogram. A slope value k was determined by linear regression of a remaining percentage of a parent drug relative to a natural logarithm of an incubation time curve.

In-vitro half-life periods ($t_{1/2}$) were respectively calculated and determined according to the slope value, and an average value of the in-vitro half-life periods was converted into an in-vitro intrinsic clearance rate (CLint, represented by μL/min/mg protein).

Experimental results are shown in the following Table 3:

TABLE 3

Stability data of the compound of the present application in liver microsomes of human, rat and mouse

| Example | $t_{1/2}$ (min) | | | $CL_{int}$ (μL/min/mg) Species | | | % Remaining(45 min) | | |
|---|---|---|---|---|---|---|---|---|---|
| | Human | Rat | Mouse | Human | Rat | Mouse | Human | Rat | Mouse |
| 1 | 8.17 | 7.35 | 16.76 | 169.73 | 188.59 | 82.72 | 4.24 | 3.30 | 16.15 |
| LOXO-195 | 16.78 | 9.12 | 7.45 | 82.65 | 152.03 | 186.01 | 16.23 | 4.88 | 1.98 |
| 2 | 16.11 | 6.50 | 13.03 | 86.01 | 213.62 | 106.46 | 14.38 | 2.37 | 9.22 |
| Positive control 1 | 15.02 | 11.27 | 17.63 | 92.30 | 123.02 | 78.63 | 12.43 | 9.03 | 16.90 |
| 3 | 127.85 | 60.77 | 43.21 | 11.11 | 22.81 | 32.10 | 69.89 | 51.22 | 39.49 |
| Positive control 2 | 84.82 | 46.29 | 18.94 | 16.36 | 29.96 | 73.23 | 67.39 | 40.95 | 11.64 |

LOXO-195 is a second generation TRK inhibitor, with the following chemical structure:

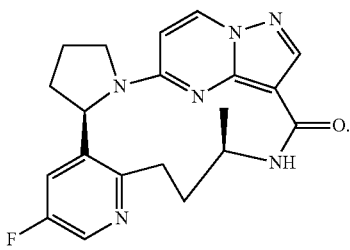

The positive control 1 is the compound in example 5 of patent WO2019210835, with the following chemical structure:

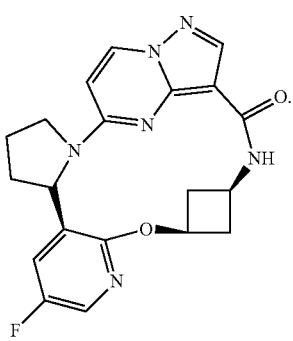

The positive control 2 is the compound in example 6 of patent WO2019210835, with the following chemical structure:

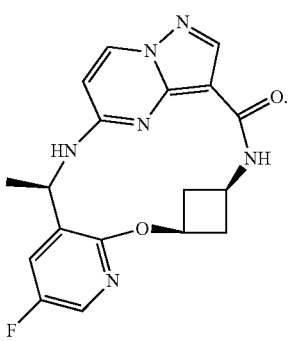 [SMILES: C[C@H]1Nc2ccn3ncc(c3n2)C(=O)N[C@H]2C[C@H](C2)Oc2ncc(F)cc21]

From data of the compound in the specific examples, the compound of the present application has a good stability in the liver microsomes of human, rat and mouse. The stabilities of the compounds in example 1 and example 2 in the liver microsomes of human, rat and mouse are not significantly different from that of the corresponding positive compound, or the stabilities of the compounds in example 1 and example 2 in the liver microsomes of most species are worse. However, the stability of the compound in example 3 in the microsomes of human, rat and mouse liver is obviously better than that of the positive control 2.

Testing Example 4

In-Vivo Pharmacokinetic Study on SD Rats Intravenously and Orally Administrated with Tested Compound 1. Experimental Animals Species: SD rats, SPF level. Source: the animals were transferred from the animal repository (999M-017) of the experimental institution of Shanghai Sippe-Bk Lab Animal Co., Ltd. Quantity: 3 rats for each formulation.

2. Preparation of Test Samples 2.1 An appropriate amount of test samples were accurately weighed, added to a final volume of 5% DMSO, 10% polyethylene glycol-15 hydroxystearate and 85% normal saline, and fully mixed by vortex or ultrasound to obtain 0.2 mg/mL administration solution for intravenous administration.

2.2 An appropriate amount of test samples were accurately weighed, added to a final volume of 5% DMSO, 10% polyethylene glycol-15 hydroxystearate and 85% normal saline, and fully mixed by vortex or ultrasound to obtain 0.5 mg/mL administration solution for oral and intragastric administration.

3. Experimental Design

| Group | Test sample | Quantity (male) | Dosage (mg/kg) | Concentration (mg/mL) | Administration volume (mL/kg) | Administration mode | Sample collection |
|---|---|---|---|---|---|---|---|
| 1 | Example 2 | 3 | 1 | 0.2 | 5 | IV | Plasma |
| 2 |  | 3 | 5 | 0.5 | 10 | PO | Plasma |
| 3 | Positive control 1 | 3 | 1 | 0.2 | 5 | IV | Plasma |
| 4 |  | 3 | 5 | 0.5 | 10 | PO | Plasma |
| 5 | Example 3 | 3 | 1 | 0.2 | 5 | IV | Plasma |
| 6 |  | 3 | 5 | 0.5 | 10 | PO | Plasma |
| 7 | Positive control 2 | 3 | 1 | 0.2 | 5 | IV | Plasma |
| 8 |  | 3 | 5 | 0.5 | 10 | PO | Plasma |

4. Administration Mode

Weighing was carried out before administration, and the dosage was calculated according to the weight. Intravenous administration, or oral intragastric administration was carried out.

5. Time Point of Blood Sampling

The blood sampling was carried out before administration and 0.083 hour, 0.25 hour, 0.5 hour, 1 hour, 2 hours, 4 hours, 6 hours, 8 hours, and 24 hours after administration.

6. Sample Collection and Disposition

The blood sampling was carried out through a jugular vein or other suitable modes, and about 0.20 mL of each sample was collected. Heparin sodium was used for anticoagulation, the collected blood samples were placed on ice, and plasma was centrifuged within 2 hours (the centrifugation was carried out by a centrifugal force of 6,800 g for 6 minutes at 2° C. to 8° C.). The collected plasma samples were stored in a refrigerator at −80° C. before analysis, and the remaining plasma samples after analysis were continuously stored in the refrigerator at −80° C. for temporary storage.

7. Biological Analysis and Data Processing

A plasma concentration of a test subject was detected, a plasma concentration-time curve was drawn, and BLQs were all recorded as 0. When pharmacokinetic parameters were calculated, a concentration before administration was calculated as 0; BLQ appearing before $C_{max}$ (comprising "No peak") was calculated as 0; and BLQ appearing after $C_{max}$ (comprising "No peak") did not participate in the calculation. According to blood concentration data at different time points, the pharmacokinetic parameters such as AUC(0-t), $T_{1/2}$ and $C_{max}$ were calculated by WinNonlin.

TABLE 4

Data of in-vivo pharmacokinetic study on SD rats intravenously and orally administered with tested compound

|  | Compound | Example 2 | Positive control 1 |
|---|---|---|---|
| IV @ 1 mg/kg | Half-life period $t_{1/2}$(h) | 0.33 | 0.45 |
|  | Concentration to peak $C_{max}$ (nM) | 875.13 | 1163.29 |
|  | Area under curve $AUC_{(0-t)}$(ng · h/mL) | 422.34 | 605.23 |
|  | Apparent clearance rate Cl(mL/min · kg) | 39.40 | 27.54 |
| PO @ 5 mg/kg | Half-life period $t_{1/2}$(h) | 0.55 | 0.68 |
|  | Concentration to peak $C_{max}$ (nM) | 527.18 | 932.14 |
|  | Area under curve $AUC_{(0-t)}$(ng · h/mL) | 1497.55 | 2273.35 |
|  | Bioavailability F % | 70.92 | 75.12 |

TABLE 4-continued

Data of in-vivo pharmacokinetic study on SD rats intravenously and orally administered with tested compound

|  | Compound | Example 3 | Positive control 2 |
|---|---|---|---|
| IV @ 1 mg/kg | Half-life period $t_{1/2}$(h) | 5.00 | 4.54 |
|  | Concentration to peak $C_{max}$ (nM) | 573.49 | 780.63 |
|  | Area under curve $AUC_{(0-t)}$(ng · h/mL) | 1477.45 | 1008.75 |
|  | Apparent clearance rate Cl(mL/min · kg) | 11.23 | 16.44 |
| PO @ 5 mg/kg | Half-life period $t_{1/2}$(h) | 3.01 | 3.00 |
|  | Concentration to peak $C_{max}$ (nM) | 1297.63 | 632.71 |
|  | Area under curve $AUC_{(0-t)}$(ng · h/mL) | 8769.13 | 3345.13 |
|  | Bioavailability F % | 118.71 | 66.32 |

The positive control 1 is the compound in example 5 of patent WO2019210835, with the following chemical structure:

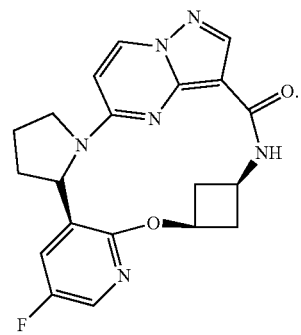

The positive control 2 is the compound in example 6 of patent WO2019210835, with the following chemical structure:

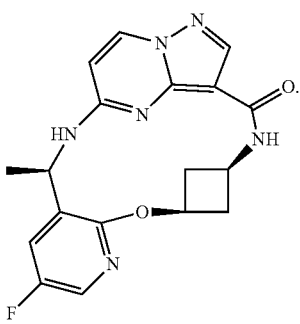 [SMILES: C[C@H]1Nc2ccn3ncc(c3n2)C(=O)N[C@H]2C[C@H](C2)Oc2ncc(F)cc21]

From data of the compound in the specific examples, the in-vivo pharmacokinetic parameters (AUC/CL/F %) of the compound in example 2 on the SD rats are worse than those of the corresponding positive compound, but the in-vivo pharmacokinetic parameters (AUC/CL/F %) of the compound in example 3 on the SD rats are unexpectedly and significantly higher than those of the positive control 2.

Compared with the positive control compound 2, efficacies and pharmacokinetics of the compound in example 3 of the present application on mutated NTRK3-G623R and NTRK1-G667C are significant improved, which can realize clinical benefits of low dosage and low administration frequency.

Testing Example 5

Bidirectional Permeability Study on Test Compound on MDCK-MDR1 Cell Line 1.1 Materials MDCK-MDR1 cells were purchased from Netherlands Cancer Institute, and cells between 10 and 20 generations were used.

1.2 Experimental Design 1.2.1 Cell Culture and Plate Inoculation

1) Before cell inoculation, 50 µL of cell medium was added into each well of an upper chamber of Transwell, and 25 mL of cell medium was added into a lower culture plate. The culture plate was placed in an incubator at 37° C. under 5% $CO_2$ for incubation for 1 hour, and then could be used for inoculating cells.

2) The MDCK-MDR1 cells were resuspended with the medium, so that a final concentration was $1.56 \times 10^6$ cells/mL. A cell suspension was added into an upper chamber of a 96-well Transwell culture plate according to 50 µL per well. The incubator was set at 37° C. under 5% $CO_2$, and was ensured to have a relative humidity of 95% for culturing for 4 days to 8 days. The medium was replaced 48 hours after inoculation, the culturing lasted for 4 days to 8 days, and the medium was replaced every other day.

1.2.2 Evaluation of Integrity of Cell Monolayer Film

1) The original medium in the lower culture plate was removed, and fresh preheated medium was added into the upper chamber.

2) A resistance of the monolayer film was measured by a resistance meter (Millipore, USA), and a resistance of each well was recorded.

3) After finishing measuring, the Transwell culture plate was put back into the incubator.

4) Calculation of resistance value: measured resistance value (ohms)×film area ($cm^2$)=TEER value (ohm $cm^2$), and if the TEER value was less than 42 ohms $cm^2$, the well could not be used for a penetration experiment.

1.2.3 Solution Preparation

1) The to-be-tested compound was prepared into 10 mM mother solution with DMSO.

2) The positive control compound was prepared into 10 mM mother solution with DMSO.

3) Metoprolol (purchased from China National Institutes for Food and Drug Control) and Digoxin (purchased from Tianjin Yifang Technology Co., Ltd.) were positive control compounds in this experiment.

1.2.4 Drug Penetration Experiment

1) The MDCK-MDR1 Transwell culture plate was taken from the incubator. The cell monolayer film was moistened and washed twice with a preheated HBSS (25 mM HEPES, pH 7.4) buffer, and incubated at 37° C. for 30 minutes.

2) A stock solution of the control compound and the test compound was diluted in DMSO to obtain a 200 µM solution, and then diluted with HBSS (10 mM HEPES, pH 7.4) to obtain a 1 µM working solution. A final concentration of DMSO in the incubation system was 0.5%.

3) A transfer rate of the compound from a top end to a base end was measured. 125 µL of working solution was added into the upper chamber (top end), then 50 µL of sample solution was immediately transferred from a lower chamber (base end) to a 96-well plate filled with 200 µL of acetonitrile containing an internal standard as a 0-minute administration sample (A-B) for detection, and 235 µL of HBSS (25 mM HEPES, pH 7.4) buffer was added into the lower chamber. The internal standard contained 100 nM alprazolam, 200 nM caffeine and 100 nM tolbutamide. The 50 µL of sample solution transferred above was vortexed at a speed of 1,000 rpm for 10 minutes.

4) A transfer rate of the compound from the base end to the top end was measured. 285 µL of working solution was added into the lower chamber (base end), then 50 µL of sample solution was immediately transferred from the upper chamber (top end) to a 96-well plate filled with 200 µL of acetonitrile containing an internal standard as a 0-minute administration sample (B-A) for detection, and 75 µL of HB SS (25 mM HEPES, pH 7.4) buffer was added into the upper chamber. The internal standard contained 100 nM alprazolam, 200 nM caffeine and 100 nM tolbutamide. The 50 µL of sample solution transferred above was vortexed at a speed of 1,000 rpm for 10 minutes. The experiment from the top end to the base end and the experiment from the base end to the top end should be carried out simultaneously.

5) After adding the buffers into the lower chamber and the upper chamber respectively, the MDCK-MDR1 Transwell culture plate was incubated at 37° C. for 2 hours.

6) After finishing incubating, 50 µL of sample solutions were respectively taken from an administration side (the upper chamber: Ap→Bl flux, the lower chamber: Bl→Ap) and a receiving side (the lower chamber: Ap→Bl flux, the upper chamber Bl→Ap) and added into new 96-well plates, and 4 times volume of ethanol containing the internal standard was added into the well plates. The internal standard substance contained 100 nM alprazolam, 200 nM caffeine and 100 nM tolbutamide. The solution was vortexed for 10 minutes, and then centrifuged at 3,220 g for 40 minutes. 100 µL of supernatant was sucked and mixed with equal volume of ultrapure water, and then subjected to LC-MS/MS analysis.

7) The integrity of the cell monolayer film after incubation for 2 hours was evaluated with the leakage of fluorescent yellow. A fluorescent yellow stock solution was diluted with HB SS (10 mM HEPES, pH 7.4) to a final concentration of 100 µM, 100 µL of fluorescent yellow solution was added into each well of the upper chamber (top end), and 300 µL of HBSS (25 mM HEPES, pH 7.4) was added into each well in a base of the lower chamber (base end). After incubation at 37° C. for 30 minutes, 80 µL of solution was respectively sucked from upper and lower layers of each well and added into a new 96-well plate. Fluorescence measurement was carried out under an excitation wavelength of 485 nm and an emission wavelength of 530 nm by a microplate reader.

1.2.5 Analysis Conditions

LC system: Shimadzu

MS analysis: Triple Quad 5500 instrument from AB Inc with an ESI interface

1) LC Parameters

Column temperature: 40° C.

Chromatographic column: Waters XSelect HSS T3 C18, 2.5 µM, 2.1×50 mm

Mobile phase: 0.1% formic acid dissolved in water (A) and 0.1% formic acid dissolved in acetonitrile (B)

Sample injection volume: 5 µL

Elution rate: 0.6 mL/min

|  | Time (min) | | | | | |
| --- | --- | --- | --- | --- | --- | --- |
|  | 0 | 0.2 | 0.7 | 1.2 | 1.25 | 1.5 |
| % B | 5 | 5 | 95 | 95 | 5 | 5 |

2) MS Parameters

Ion source: Turbo spray

Ionization model: ESI

Scan type: Multi-reaction monitoring (MRM)

Curtain gas: 35 L/min

Collision gas: 9 L/min

Carrier gas: 50 L/min

Auxiliary gas: 50 L/min

Temperature: 500° C.

Ionspray voltage+5500 V (positive)

1.3 Data Analysis

A peak area was calculated according to results of ion chromatography. An apparent permeability coefficient (Papp, unit: cm/s×10$^{-6}$) of the compound was calculated by the following formula:

$$P_{app} = \frac{V_A}{Area \times time} \times \frac{[drug]_{acceptor}}{[drug]_{initial,donor}}$$

wherein $V_A$ was a volume of the solution at the receiving end (Ap→Bl was 0.3 mL, Bl→Ap was 0.1 mL); Area was a film area of the Transwell-96-well plate (0.143 cm$^2$); time was an incubation time (unit: s); and [drug] was a drug concentration.

Experimental results are shown in the following Table 5:

TABLE 5

| Data of bidirectional permeability study on test compound on MDCK-MDR1 cell line in the same batch | | | |
| --- | --- | --- | --- |
| Number of example | $P_{app\ (A-B)}$ ($10^{-6}$, cm/s) | $P_{app\ (B-A)}$ ($10^{-6}$, cm/s) | Excretion ratio* |
| Example 3 | 11.13 | 51.91 | 4.67 |
| Positive control 2 | 3.31 | 64.41 | 19.42 |

*Excretion ratio = $P_{app\ (B-A)}/P_{app\ (A-B)}$

The positive control 2 is the compound in example 6 of patent WO2019210835, with the following chemical structure:

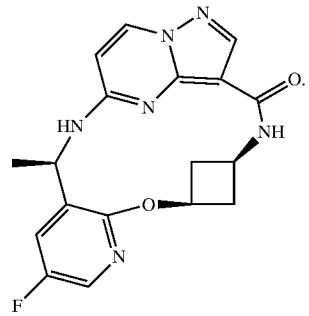 [SMILES: C[C@H]1Nc2ccn3ncc(c3n2)C(=O)N[C@H]2C[C@H](C2)Oc2ncc(F)cc21]

The permeability ($P_{app(A-B)}$) of the compound in example 3 is better than that of the positive control 2, which indicates that the compound in example 3 is easier to be absorbed into cells. Meanwhile, the compound in example 3 has a low excretion ratio, which indicates that the compound in example 3 is not easy to be excreted, thus maintaining a high drug concentration in cells and producing better efficacy. Therefore, in combination with the in-vivo pharmacokinetic study on the SD rats, the in-vivo pharmacokinetic parameters (AUC/CL/F %) of the compound in example 3 on the SD rats are unexpectedly and significantly higher than those of the positive control 2.

Testing Example 6

In-Vitro Cell Viability

Hefei Precedo Biomedical Technology Co., Ltd. was commissioned to complete the testing example, and the cell lines used were constructed by this company.

1. Experimental Purpose

In-vitro anti-proliferative effects of the compound of the present application on 6 BaF3 cell lines were measured.

2. Reagents and Consumables

Cell Line:

| Cell line | Cell type | Quantity of cells/well | Medium |
| --- | --- | --- | --- |
| Ba/F3-LMNA-NTRK1 | Suspension | 2000 | RPMI 1640 + 10% FBS + 1% PS |
| Ba/F3-LMNA-NTRK1-V573I | Suspension | 2000 | RPMI 1640 + 10% FBS + 1% PS |
| Ba/F3-LMNA-NTRK1-F589L | Suspension | 2000 | RPMI 1640 + 10% FBS + 1% PS |

-continued

| Cell line | Cell type | Quantity of cells/well | Medium |
|---|---|---|---|
| Ba/F3-LMNA-NTRK1-G667S | Suspension | 2000 | RPMI 1640 + 10% FBS + 1% PS |
| Ba/F3-TEL-NTRK2 | Suspension | 2000 | RPMI 1640 + 10% FBS + 1% PS |
| Ba/F3-TEL-NTRK3 | Suspension | 2000 | RPMI 1640 + 10% FBS + 1% PS |

Materials:

| Catalogue | Brand | Item number | Batch number |
|---|---|---|---|
| RPMI 1640 | BI | 01-100-1acs | 0023019 |
| Fetal bovine serum | BI | BI04-001-1ACS | 1616756 |
| Penicillin-streptomycin solution | Corning | 30-002-CI | 30002311 |
| Interleukin-3 | Novusbio | NBP2-35123 | N12103071 |
| CellTiterGlo | Promega | G7573 | 347569 |
| Trypanblue | Solarbio | C0040 | 20181024 |
| 96-well white plate | Corning | 3917 | 33917037 |
| 96-well drug plate | Beaver | 40196 | 18C006004 |
| Loading slot | Corning | 4870 | 10519072 |
| 10 μl tip | Axygen | T-300 | 00518391 |
| 200 μl tip | Sangon | F600227 | F617LA2491 |
| 1,000 μl tip | Excell | CS015-0031 | 190486 |
| 50 ml centrifuge tube | NEST | 602052 | 111918EE01 |
| 15 ml centrifuge tube | NEST | 601052 | 051819EE02 |
| Dimethyl sulfoxide | TCI | D5293 | 64Y4N-DS |

3. Experimental Process
Cell Processing and Administration
Cell Culture Conditions 6 Ba/F3 cell lines were cultured with RPMI 1640 (Biological Industries, Israel)+10% fetal calf serum (Biological Industries, Israel)+1% double antibiotics (Penicillin Streptomycin solution, Coring, USA), and cells were cultured for two generations after resuscitation, to be tested.

Preparation of 1,000× Compounds

The to-be-tested compound was prepared into 10 mM mother solution with DMSO, and then diluted to 1 mM with DMSO. The solution was diluted by 3 times to prepare into 1.0000 mM, 0.3333 mM, 0.1111 mM, 0.03704 mM, 0.01235 mM, 0.00412 mM, 0.00137 mM, 0.00015 mM, 0.00015 mM, and 0.0005 mM, and stored in a 96-well drug plate (Beaver, Suzhou), with 10 concentration gradients in total. Meanwhile, an equal volume of DMSO solvent was used as a negative control.

Preparation of 20× Compounds

The prepared 1,000× compounds of 10 concentration gradients were respectively diluted by 50 times into 20× compounds with complete medium, and stored in a 96-well drug plate (Beaver, Suzhou), with 10 concentration gradients in total. Meanwhile, an equal volume of DMSO solvent was used as a negative control.

Cell Plating

Cell suspension in logarithmic growth phase was inoculated on a 96-well white cell culture plate (Corning 3917, NY, USA), and a volume of each well was 95 μl (about 2000 cells/well).

5 μl of 20× to-be-tested compounds were respectively added into the culture plate containing 95 μl of cell suspension above, and mixed evenly, with 2 wells for each concentration gradient. Final concentrations of the to-be-tested compounds were 1.0000 μM, 0.3333 μM, 0.1111 μM, 0.03704 μM, 0.01235 μM, 0.00412 μM, 0.00137 μM, 0.00046 μM, 0.00015 μM, and 0.0005 μM respectively.

Incubation was carried out in an incubator at 37° C. under 5% $CO_2$ for 72 hours.

Plate Reading

The following steps were carried out according to the instruction of Promega CellTiter-Glo Luminescence Cell Viability Assay Kit (Promega-G7573).

(1). A CellTiter-Glo buffer was melted and placed at room temperature.

(2). A CellTiter-Glo substrate was plated at room temperature.

(3). The Celtiter-Glo buffer was added into a bottle of Celtiter-Glo substrate to dissolve the substrate, thus preparing a Celtiter-Glo working solution.

(4). The substrate was fully dissolved by slow vortex oscillation.

(5). The cell culture plate was taken out and placed for 10 minutes to balance to room temperature.

(6). 50 μl of CellTiter-Glo working solution was added into each hole.

(7) The culture plate was shaken on an orbital shaker for 2 minutes to induce cell lysis.

(8). The culture plate was placed at room temperature for 10 minutes to stabilize a luminous signal.

(9). The luminous signal was detected on a MD SpectraMax Paradigm plate reader.

Data Analysis

A corresponding fluorescence value RLU of each well was obtained through reading by SpectraMax Paradigm. Cell viability data was processed by the following formula:

Cell viability(%)=$(RLU_{Drug}-RLU_{Min})/(RLU_{Max}-RLU_{Min})*100\%$. Cell viabilities of compounds of different concentrations were calculated in EXCEL, then cell viability curves were made by GraphPad Prism software, and related parameters were calculated. The parameters comprised a maximum cell viability, a minimum cell viability, and an $IC_{50}$ value.

Experimental results are shown in the following Table 6:

TABLE 6

$IC_{50}$ values of inhibitory activities of the compound of the present application on 6 BaF3 cell lines in the same batch

| | $IC_{50}$ (nM) of compound | | | |
|---|---|---|---|---|
| Cell line | Example 2 | Positive control 1 | Example 3 | Positive control 2 |
| Ba/F3-LMNA-NTRK1 | 0.7 | 0.5 | 1.6 | 4.1 |
| Ba/F3-LMNA-NTRK1-V573I | 0.3 | 0.2 | 1.1 | 2.3 |
| Ba/F3-LMNA-NTRK1-F589L | 2.4 | 6.6 | 1.2 | 4.5 |
| Ba/F3-LMNA-NTRK1-G667S | 3.4 | 2.7 | 8.4 | 19.9 |
| Ba/F3-TEL-NTRK2 | 1.6 | 0.9 | 3.4 | 7.3 |
| Ba/F3-TEL-NTRK3 | 1.7 | 0.9 | 5.0 | 9.8 |

The positive control 1 is the compound in example 5 of patent WO2019210835, with the following chemical structure:

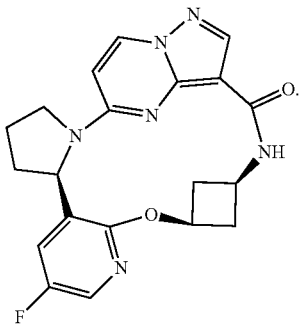 [SMILES: O=C1N[C@H]2C[C@H](C2)Oc2ncc(F)cc2[C@H]2CCCN2c2ccn3ncc1c3n2]

The positive control 2 is the compound in example 6 of patent WO2019210835, with the following chemical structure:

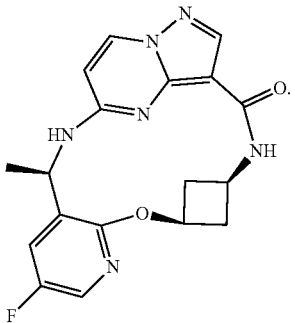 [SMILES: C[C@H]1Nc2ccn3ncc(c3n2)C(=O)N[C@H]2C[C@H](C2)Oc2ncc(F)cc21]

From biological activity data of the compound in the specific examples, the compound of the present application has strong growth inhibition effects on 6BaF3 cell lines. The inhibitory activities of the compound in example 2 on 6BaF3 cell lines are not significantly different from those of the corresponding positive compound, but the inhibitory activities of the compound in examples 3 of the present application on 6BaF3 cell lines are significantly higher than those of the corresponding positive control 2.

It will be appreciated by those skilled in the art that changes could be made to the embodiment described above without departing from the broad inventive concept thereof. It is understood, therefore, that this invention is not limited to the particular embodiment disclosed, but it is intended to cover modifications within the spirit and scope of the present invention as defined by the appended claims.

The invention claimed is:

1. A compound of formula (I), a tautomer, a mesomer, a racemate, an enantiomer, a diastereomer or a mixture thereof, or a pharmaceutically acceptable salt thereof:

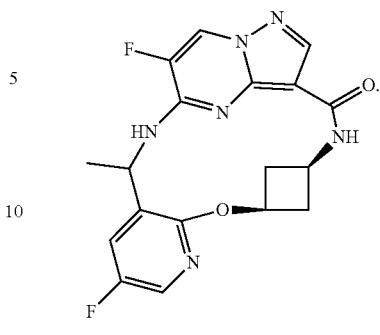

(I)

2. The compound of formula (I), the tautomer, the mesomer, the racemate, the enantiomer, the diastereomer or the mixture thereof, or the pharmaceutically acceptable salt thereof according to claim 1, wherein the compound is in a form of a compound of formula (Ia) or (Ib), a tautomer, a mesomer, a racemate, an enantiomer, a diastereomer or a mixture thereof, or a pharmaceutically acceptable salt thereof:

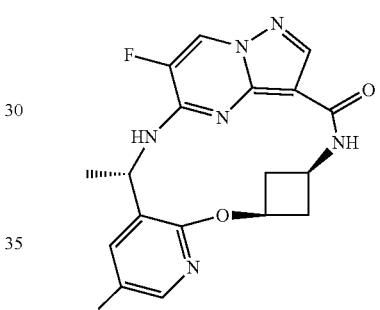

(Ia)

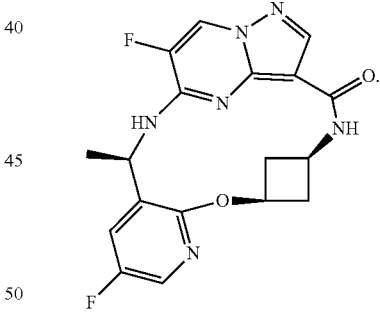

(Ib)

3. A pharmaceutical composition, comprising the compound, the tautomer, the mesomer, the racemate, the enantiomer, the diastereomer or the mixture thereof, or the pharmaceutically acceptable salt thereof according to claim 1, and a pharmaceutically acceptable diluent or carrier.

4. A method of inhibiting an activity of a TRK kinase, comprising administrating the compound, the tautomer, the mesomer, the racemate, the enantiomer, the diastereomer or the mixture thereof, or the pharmaceutically acceptable salt thereof according to claim 1, or the pharmaceutical composition thereof to a subject in need thereof.

* * * * *